Figure 1:
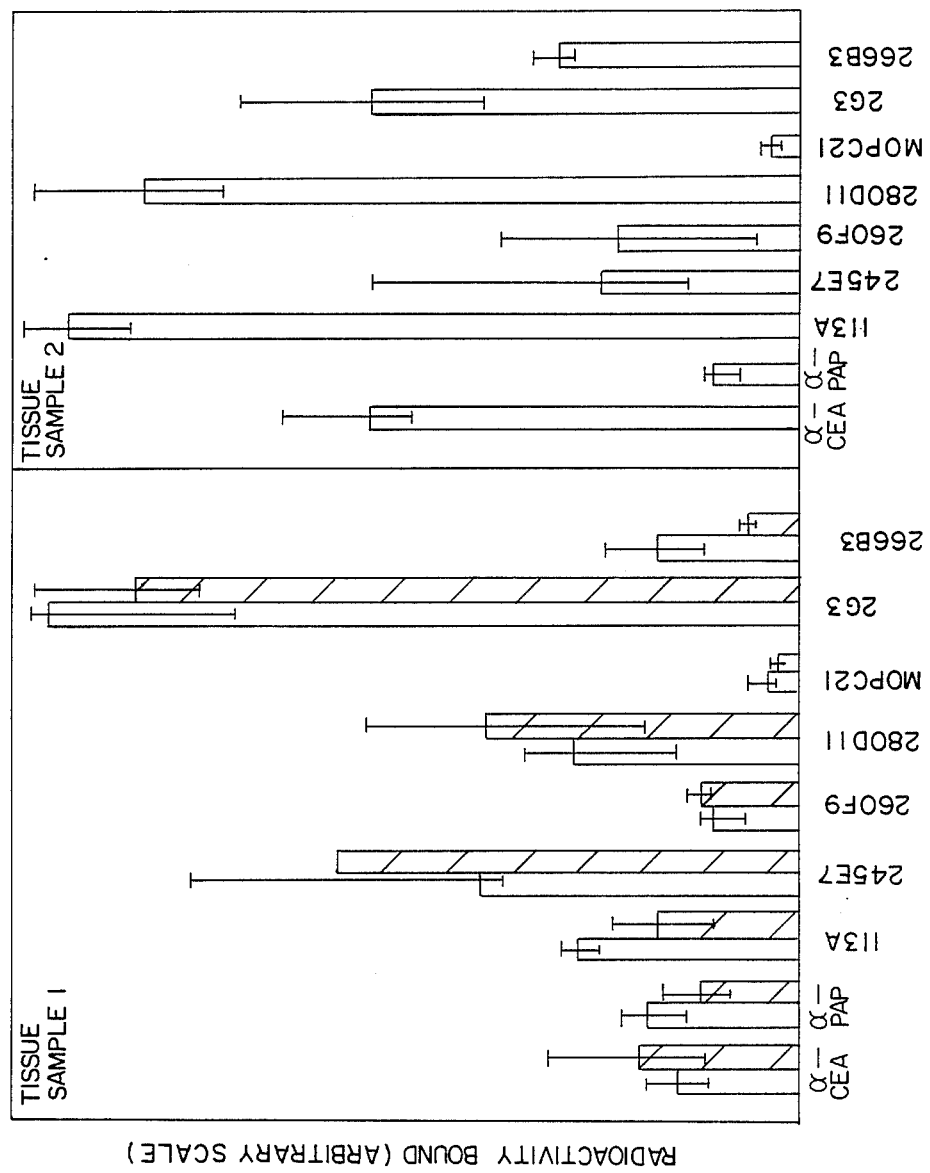
Figure 2:
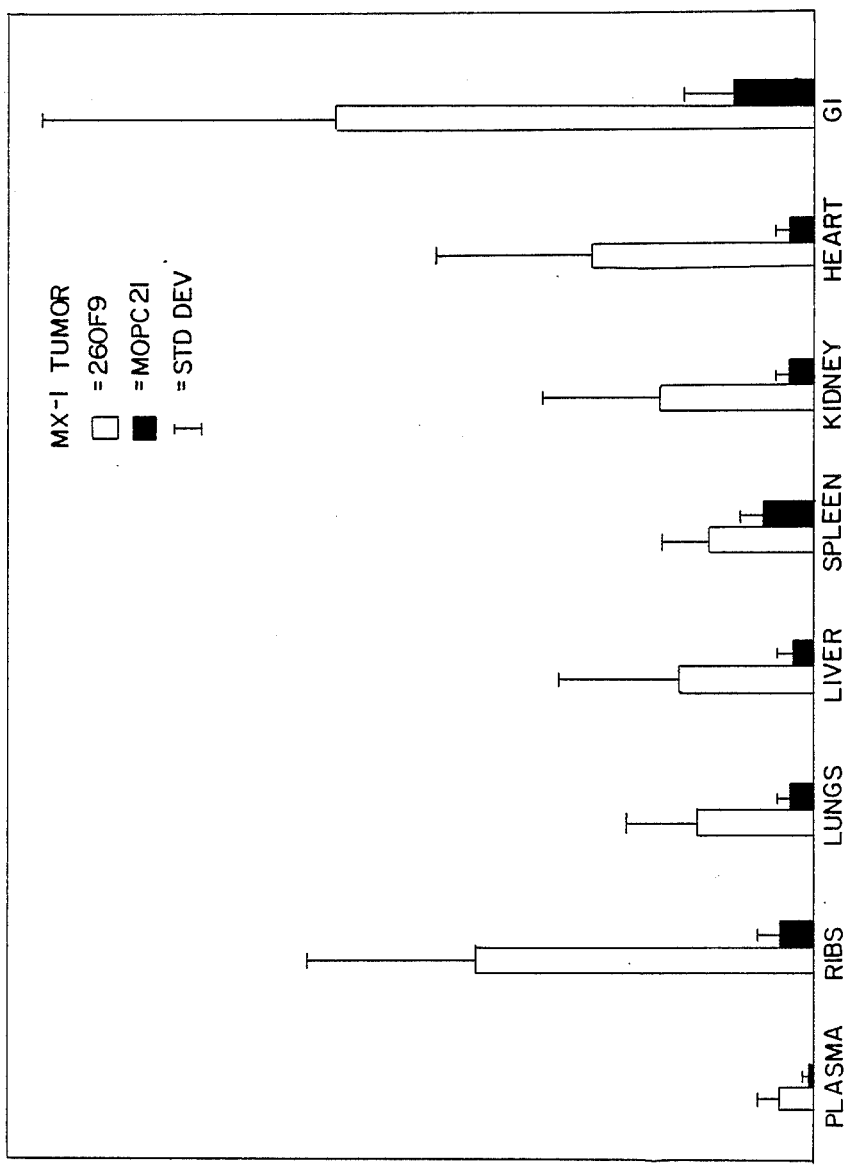

United States Patent [19]

Ring et al.

[11] Patent Number: 4,938,948

[45] Date of Patent: Jul. 3, 1990

[54] METHOD FOR IMAGING BREAST TUMORS USING LABELED MONOCLONAL ANTI-HUMAN BREAST CANCER ANTIBODIES

[75] Inventors: David B. Ring, Redwood City, Calif.; Arthur E. Frankel, Durham, N.C.

[73] Assignee: Cetus Corporation, Emeryville, Calif.

[21] Appl. No.: 786,948

[22] Filed: Oct. 11, 1985

Related U.S. Application Data

[63] Continuation-in-part of Ser. No. 785,076, Oct. 7, 1985, abandoned.

[51] Int. Cl.$^5$ .................... A61K 49/02; A61K 49/00
[52] U.S. Cl. ......................................... 424/9; 424/4; 424/85.8; 435/172.2; 435/948; 935/102; 935/107; 935/808; 530/387; 530/402; 530/808
[58] Field of Search ..................... 435/7, 172.1, 172.2, 435/240; 436/547, 548; 424/9, 4

[56] References Cited

U.S. PATENT DOCUMENTS

| | | |
|---|---|---|
| 4,522,918 | 6/1985 | Schlom et al. |
| 4,695,538 | 9/1987 | Cote et al. ............... 436/536 |
| 4,707,438 | 11/1987 | Keydar ..................... 435/5 |
| 4,753,894 | 6/1988 | Frankel et al. |

OTHER PUBLICATIONS

Colcher et al.—Chem. Abst. vol. 101 (1984) p. 168715q.
Neville et al.—Chem. Abst. vol. 101 (1984) p. 157653s.
Brabon et al.—Chem. Abst. vol. 101 (1984) p. 21734m.
Colcher, D. et al., Proc. Natl. Acad. Sci., vol. 78, pp. 3199-3203 (1981).
Yuan D., et al., JNCL., vol. 68, (1982).
Ciocca, D. R., et al., Cancer Research, vol. 42, pp. 4256-4258 (1982).
Kohler and Milstein, Nature vol. 256, pp. 495-497 (1975).
Buck, D. W., et al., In Vitro, vol. 18, pp. 377-381 (1982).
Wood, F. T., et al., Analytical Biochemistry, vol. 69, pp. 339-349 (1975).
Goodwin, D. A. et al., J. Nucl. Med., 26:493-503, (1985).
Meares, C. F., et al., Analytical Biochemistry, vol. 142, pp. 68-78 (1984).
Levine, G., et al., The Journal of Nuclear Medicine, vol. 21, pp. 570-573 (1980).
Ferrands, P. A., et al., The Lancet, (1982).
Zimmer, A. M., et al., Hybridoma, vol. 4, pp. 1-11, (1985).
Contreras, M. A., et al., Methods in Enzymology, vol. 92, pp. 277-292 (1983).
Khaw, B. A., et al., Hybridoma, vol. 3, pp. 11-23 (1984).
Krejcarek, G. E., et al., Biochemical and Biophysical Research Communications, vol. 77, pp. 581-585 (1977).
Hnatowich, D. J., et al., Science, vol. 220, pp. 613-615 (1983).
Scheinberg, D. A., et al., Science, vol. 215, pp. 1511-1513 (1982).
Thompson, C. H., et al., The Lancet, pp. 1245-1247 (1984).
Mach, J. P., et al., Cancer Research, vol. 43, pp. 5593-5600, (1983).
Murray, J. L., et al., Cancer Research, vol. 45, pp. 2376-2381, (1985).
Rosenblum, M. G., et al., Cancer Research, vol. 45, pp. 2382-2386, (1985).
Halpern, S. E., et al., Cancer Research, vol. 43, pp. 5347-5355, (1983).
Hnatowich, D. J., 1984 Abstract Form for Scientific Papers & Scientific Exhibits Society of Nuclear Medicine 31st Annual Meeting, Los Angeles, CA, Jun. 5-8-, 1984.
Burchell, J. et al., The Journal of Immunology, vol. 131, pp. 508-513 (1983).

*Primary Examiner*—Sam Rosen
*Attorney, Agent, or Firm*—Gregory J. Giotta; Elliott E. Fineman; Albert P. Halluin

[57] ABSTRACT

Hybridomas producing monoclonal antibodies suitable for imaging and diagnosis of human breast tumors and such monoclonal antibodies are claimed. The monoclonals are characterized by breast tumor binding range, breast cancer cell line range, and selectivity.

Immunoimaging agents comprising the monoclonal antibody and a detectable label, either directly or indirectly conjugated to the antibody are claimed. Methods for imaging breast tumors using the immunoimaging agents are described and claimed.

9 Claims, 3 Drawing Sheets

TUMOR/ORAN RATIOS ically it con-
METHOD FOR IMAGING BREAST TUMORS USING LABELED MONOCLONAL ANTI-HUMAN BREAST CANCER ANTIBODIES This patent application is a continuation-in-part application of copending U.S. Application Ser. No. 785,076 filed Oct. 7, 1985, now abandoned.

DESCRIPTION

1. Technical Field

This invention is in the fields of immunology and cancer diagnosis and therapy. More particularly it concerns murine monoclonal anti-human breast cancer antibodies, hybridomas that produce those antibodies, immunochemicals made from those antibodies, and diagnostic and therapeutic methods that use those immunochemicals.

2. Background Art

Since the mid-1970s, there have been numerous reports of murine monoclonal antibodies that interact with human breast cancer associated antigens. In these reported studies, mice were immunized and boosted with human milk fat globule proteins, breast cancer cell lines or breast cancer membrane extracts. Immune splenocytes were fused with mouse myeloma cells and hybridomas were selected based on some specificity of the culture media for breast or breast cancer antigens. Taylor-Papadimitriou, J., et al, *Int. J. Cancer* (1981) 28:17–21; Yuan, D., et al, JNCI (1982) 68:719–728; Ciocca, D. R., et al, Cancer Res. (1982) 42:4256–4258. The normal tissue reactivities of these prior antibodies are different than the normal tissue reactivities of the antibodies of the present invention.

A principal aspect of the invention concerns murine monoclonal antibodies that:
(a) do not bind to blood cells;
(b) have a breast tumor binding range of at least 0.25 or have a breast cancer cell line binding range of greater than or equal to 0.25;
(c) have a selectivity equal to or less than 0.09;
(d) have a G or M isotype, and
(e) when conjugated to an imaging moiety, produce a signal sufficient to image breast cancer tumors.

Preferred embodiments of these antibodies are those designated 2G3, 9C6, 32A1, 33F8, 35E10, 41B4, 87H7, 106A10, 113F1, 120H7, 140A7, 200F9, 203E2, 219F3, 245E7, 254H9, 260F9, 266B2, 317G5, 369F10, 387H9, 421E8, 451C3, 452E12, 452F2, 454A12, 454C11, 457D7, 520C9, 650E2, 697B3, 741F8, 759E3, 788G6, and functional equivalents thereof.

The murine x murine hydridomas that produce the above described antibodies and progeny of those hybridomas are other aspects of the invention.

Another aspect of the invention relates to immunoimaging agents that are conjugates of
(a) the above described monoclonal antibodies, and
(b) a detectable imaging moiety.

Another aspect of the invention concerns methods of imaging breast tumors in a patient in need of such imaging by administering an imaging effective amount of an immunoimaging agent and detecting the immunoimaging agent in the patient with a suitable detecting device.

MODES FOR CARRYING OUT THE INVENTION

As used herein, the term "monoclonal antibody" means an antibody composition having a homogeneous antibody population. It is not intended to be limited as regards the source of the antibody or the manner in which it is made.

As used herein with regard to the monoclonal antibody-producing hybridomas of the invention the term "progeny" is intended to include all derivatives, issue, and offspring of the parent hybridoma that produce the monoclonal anti-human breast cancer antibody produced by the parent, regardless of generation or karyotypic identity.

As used herein with respect to the exemplified murine monoclonal anti-human breast cancer antibodies, the term "functional equivalent" means a monoclonal antibody that: (a) binds to the same antigen or epitope as an exemplified monoclonal antibody; (b) has a breast tumor binding range of at least 0.25 or has a breast cancer cell line range of greater than or equal to 0.25; (c) has a selectivity equal to or less than 0.09; (d) has a G or M isotype, and (e) when conjugated to an imaging moiety, produces a signal sufficient to image breast cancer tumors.

As described above, the term "functional equivalent" as used herein includes five criteria. The first of these criteria, binding to the same antigen or epitope as an exemplified monoclonal antibody may be demonstrated by experiments which show crossblocking of an exemplified monoclonal antibody by the functionally equivalent monoclonal antibody. Crossblocking occurs as a result of an antibody binding to the same epitope on an antigen as that bound by one of the exemplified antibodies, or as a result of an antibody binding to a different epitope which is so closely situated on the same antigen that binding of an antibody to one epitope blocks the binding of an antibody to the second epitope. Crossblocking thus is one of the criteria by which one can determine that a functionally equivalent monoclonal antibody binds to the same antigen or epitope as an exemplified monoclonal antibody.

So-called "sandwich" assays are another method for determining whether an antibody binds the same antigen or epitope. In these assays, a first monoclonal antibody is bound to a support, for example, the surface of a titre plate well. After treatment to prevent nonspecific binding, a highly solubilized antigen preparation is added to the bound antibody. Subsequently, a second antibody, having a detectable label, for example, a fluorescent dye, is added. If the second antibody binds to the antigen, a different epitope specificity or multiple copies of the same epitope on the same antigen is indicated. If the second antibody fails to bind, either the same epitope specificity or different antigen specificity is indicated. The results of both the crossblocking and sandwich assay are further defined by a second series of tests such as immune precipitation or Western blotting to show that the antigen bound by both antibodies has the same molecular weight.

MONOCLONAL ANTIBODY PRODUCTION

The antibody-producing fusion partners that are used to make the hybridomas of this invention are generated by immunizing mice with live human breast cancer cells or membrane extracts made therefrom. The mice are inoculated intraperitoneally with an immunogenic amount of the cells or extract and then boosted with similar amounts of the immunogen. Spleens are collected from the immunized mice a few days after the final boost and a cell suspension is prepared therefrom for use in the fusion.

Hybridomas are prepared from the splenocytes and a murine tumor partner using the general somatic cell hybridization technique of Kohler, B. and Milstein, C., *Nature* (1975) 256:495–497 as modified by Buck, D. W., et al, In Vitro (1982) 18:377–381. Available murine myeloma lines, such as those from the Salk Institute, Cell Distribution Center, San Diego, Calif., USA, may be used in the hybridization. Basically, the technique involves fusing the tumor cells and splenocytes using a fusogen such as polyethylene glycol. After the fusion the cells are separated from the fusion medium and grown in a selective growth medium, such as HAT medium, to eliminate unhybridized parent cells. The hybridomas are expanded, if desired, and supernatants are assayed for anti-human breast cancer activity by conventional immunoassay procedures (e.g., radioimmunoassay, enzyme immunoassay, or fluorescence immunoassay) using the immunizing agent (breast cancer cells or membrane extract) as antigen. Positive clones are characterized further to determine whether they meet the criteria of the antibodies according to the invention.

Hybridomas that produce such antibodies may be grown in vitro or in vivo using known procedures. The monoclonal antibodies may be isolated from the culture media or body fluids, as the case may be, by conventional immunoglobulin purification procedures such as ammonium sulfate precipitation, gel electrophoresis, dialysis, chromatography, and ultrafiltration, if desired.

MONOCLONAL ANTIBODY SELECTION/CHARACTERIZATION

The important characteristics of the monoclonal antibodies are (1) their immunoglobulin class, (2) their selectivity for human breast cancer cells, (3) the range of human breast cancer tumor cells to which they bind, (4) the range of human breast tumor frozen sections to which they bind, and (5) their usefulness in making effective anti-human breast cancer immunoimaging agents.

The selectivity and range of a given antibody is determined by testing it against panels of (1) human breast cancer tumor tissues, (2) human breast cancer cell lines, and (3) normal human tissue or cells of breast or other origin. In selecting the claimed antibodies, approximately 22,000 growing hybridoma cultures were initially screened against the immunizing breast tumor membranes or cell line, a panel of seven normal tissues membranes, a fibroblast cell line and a breast tumor frozen section. Clones that reacted with the neoplastic materials, but not the normal materials, were identified in this initial screen and chosen for isotyping and additional screening for selectivity and range. The additional screening involved: sixteen normal tissue sections, five normal blood cell types, eleven nonbreast neoplasm sections, twenty-one breast cancer sections and fourteen breast cancer cell lines.

For purposes of this patent application, specificity and selectivity are used interchangeably and are defined as the sum of the number of substructures stained in sixteen normal tissue frozen sections and the number of blood cell types bound, divided by the sum of the total number of substructures bound by any of the monoclonal antibodies in all the tissue on which the monoclonal antibodies were tested and five blood cell types tested.

The term "tumor range' is defined as the number of breast tumor frozen sections stained divided by the number of breast tumor frozen sections tested. The term breast cancer "cell line range" is defined as the number of breast cancer cell lines stained divided by the number of breast cancer cell lines tested. Antibodies were deemed to be appropriate for breast cancer immunoimaging purposes if they have a selectivity equal to or less than 0.09 and a breast tumor binding range of equal to or greater than 0.25 or a breast cancer cell line binding range of equal to or greater than 0.25.

Antibodies exhibiting acceptable selectivity and range may be conjugated to various imaging moieties such as radioisotopes or materials detectable by nuclear magnetic resonance imaging. In some cases a coupling agent, such as a chelating agent may be used to link the imaging agent to the antibody.

Antibodies of five of the thirty-three deposited hybridomas were found to recognize the same 200 K dalton antigen. Antibodies of four of the thirty-three bound to a 230 K dalton intracellular antigen. Three bind to one or more high molecular weight mucins (HMW) and two bound to transferrin receptors in the form of a 97 K dalton antigen. All antigen weights mentioned herein were determined by sodium dodecyl sulfate (SDS) polyacrylamide gel electrophoresis under reducing conditions using procedures known in the art.

Further details of the characterization of these antibodies are provided in the examples below.

IMMUNOCHEMICALS

The immunochemical derivatives of the monoclonal antibodies of this invention that are of prime importance are labeled with an imaging moiety such as radioisotopes, radiopaque substances or nuclear magnetic resonance detectable materials. Such immunochemical derivatives, in which the imaging moiety provides a means for identifying immune complexes that invlude the labeled antibody may be used in imaging breast cancer tumors in vivo.

Antibodies that exhibit either a breast cancer tumor binding range of at least 0.25 or a breast cancer cell line binding range of at least 0.25, and that also exhibit a selectivity equal to or less than 0.09 and do not bind to blood cells, were considered selective for breast cancer immunoimaging purposes, and may be conjugated to a detectable imaging moiety. Such imaging moieties may be directly bound to the monoclonal antibody or may be bound to the monoclonal antibody by means of a linking or chelating agent. Derivatives of the monoclonal antibody, labeled wth the imaging moieties, can be made by a variety of methods well known in the art. Such labeled derivatives are also referred to herein as immunoimaging agents.

Radioisotopes of iodine may be used to iodinate monoclonal antibodies using the solid phase oxidizing agent, 13,4,6-tetrachloro-3α,6α-diphenylglycouril (sold under the tradename Iodo-gen ™ ), or N-chloro-p-toluene sulfonamide (chloramine T).

The term "linkers" used herein is intended to encompass chemical entities which may be bound to the imaging moiety and which also bind to the monoclonal antibody. Appropriate linkers may include those which bind to the monoclonal antibody and chelate radionuclides. Other linkers, such as those which may selectively bind to the carbohydrate carrying regions of the monoclonal antibody, or those that are capable of binding free amino side groups of the protein region of the monoclonal antibody, such as amidinating or imidinating agents, and which can be covalently linked to the imaging moiety, are also included in the scope of the term linker as used herein.

Appropriate linkers will have three characteristics. First, they must be capable of binding the imaging moiety which has the desired characteristic to be read for imaging. Secondly, the linker must not significantly affect the binding selectivity of the monoclonal antibody or substantially diminish its affinity for the antigen to be bound. Lastly, the linker must form a stable bond with the imaging moiety and the monoclonal antibody so that the imaging moiety and antibody will not be separated from one another.

The particular linker and imaging moiety used to make the immunoimaging agents of the present invention will vary from antibody to antibody depending on the effect that a particular imaging moiety or imaging moiety and linker may have upon the binding characteristics of the monoclonal antibody for the target antigen. Thus, while one monoclonal antibody may be iodinated with a radioisotope of iodine at tyrosine residues within the monoclonal antibody without significantly affecting affinity or selectivity of the monoclonal antibody, the same treatment of a second monoclonal antibody according to the invention may significantly diminish the affinity or binding specificity of another monoclonal antibody. A different label or linker, for example, one that binds to the antibody at a different amino acid residue, may be used without affecting selectivity or affinity in the second antibody. Thus, iodine radioisotopes can be linked to the second antibody, for example, using the method of Wood, F. T., et al. *Analy. Biochem.* 69:339 (1975) and the linker methyl-p-hydroxybenzimidate or the method of Bolton-Hunter, Bolton, A. E. and Hunter, W. M., *Biochem. J.* 133:529–539 (1973) and the linker N-succinimidyl-3-(4-hydroxyphenyl) propionate. A chelating agent such as diethylinetriaminepentaacetic acid anhydride which binds to lysine residues of the antibody, or ethylenetriaminetetraacetic acid may be used to label the antibody with 111-Indium (111-In), and could also be employed as an alternative means for linking the antibody to the imaging moiety. See for example, Goodwin, et al., "Chelate Conjugates of Monoclonal Antibodies for Imaging Lymphoid Structures in the Mouse", *J. Nucl. Med.* 26(5):493–502 (1985) and Meares et al., "Conjugation of Antibodies With Bifunctional Chelating Agents Bearing Isothiocyanate or Bromoactamide Groups and Subsequent Addition of Metal Ions", *Analy. Biochem.* 142:68–78 (1984).

Various moieties suitable for imaging are known. For example, monoclonal antibodies have been radiolabeled with a number of radionuclides suitable for imaging, including 131-iodine (I-131) and I-123. Levin et al., "Localization of I-131 Labeled Tumor Bearing Balb/c Mouse", *J. Nuclear Medicine,* 21:570–572 (1980); Farrands et al., "Radioimmunodetection of Human Colorectal Cancers by an Anti-Tumor Monoclonal Antibody", *Lancet* 397–399 (1982); Zimmer et al., "Radioimmunoimaging of Human Small Cell Lung Carcinoma With I-131 Tumor Specific Monoclonal Antibody", *Hybridoma,* 4(1):1–11 (1985). The direct labeling of the monoclonal antibody with radioisotopes of iodine can be carried out according to the methods described in Contreras et al, *Methods in Enzymology* (1973) 97:277. Technetium-99 has been used as an imaging moiety; Khaw et al., "Monoclonal Antibody to Cardiac Myosin:Imaging of Experimental Myocardial Infraction", *Hybridoma* 3:11–23 (1984). 111-In has been applied as a label for antibodies, Krejack et al., "Covalent Attachment of Chelating Groups to Macromolecules", *Biochem. Biophys. Res. Comm.,* 77:581–585 (1977); Hnatowich et al., "Radioactive Labeling of Antibody A Simple and Efficient Method", *Science,* 220:613–615 (1983) and Schienberg, D. A. et al., "Tumor Imaging With Radioactive Metal Chelates Conjugated to Monoclonal Antibodies", *Science,* 215:1151–1513 (1982).

In order to initially assess the suitability of the antibody as one appropriate for imaging, the antibody may be labeled with a moiety that is directly detectable such as fluorochromes, as well as moieties, such as enzymes, that must be reacted or derivatized to be detected. Examples of such labels are fluorescein and its derivatives, rhodamine and its derivatives, dansyl groups, umbelliferone luciferin, 2,3-dihydrophthalazinediones, horseradish peroxidase, alkaline phosphatase, lysozyme, and glucose-6-phosphate dehydrogenase. The antibodies may be tagged with such labels by known methods. For instance, coupling agents such as aldehydes, carbodiimides, dimaleimide, imidates, succinimides, bis-diazotized benzidine and the like may be used to tag the antibodies with the above-described fluorescent, chemiluminescent, and enzyme labels.

The antibodies and labeled antibody may be used in a variety of immunoimaging or immunoassay procedures to detect the presence of breast cancer in a patient or monitor the status of such cancer in a patient already diagnosed to have it. When used for in vivo immunoimaging to detect the presence of a tumor, its location and dissemination in a patient's body and the progress of therapy to ameliorate the tumor load, the monoclonal antibody labeled with an imaging moiety will be administered parenterally, preferably intravenously or subcutaneously in an amount sufficient to accumulate at the tumor site and be detected by the detecting means of choice. Typically the monoclonal antibody labeled with an imaging moiety will be administered with a suitable pharmaceutically acceptable carrier of the type well known to those skilled in the art. Such carriers do not affect the patient. The amount of monoclonal antibody to be administered will depend upon the amount of detectable imaging moiety attached to the monoclonal antibody and the residual binding efficiency of the monoclonal antibody after labeling with the imaging moiety.

The residual binding efficiency of the monoclonal antibody labeled with the imaging moiety is determined in vitro using a tumor cell binding assay. Generally, radioimmunoreactivity, which measures the residual binding efficiency of a radioisotope-labeled monoclonal antibody is determined by comparing specific binding of the radioisotope-labeled monoclonal to a fixed tissue culture of a known immunoreactive tumor cell line such as SKBR-3, MCF-7, and MX-1 with non-specific binding to a fixed cell line which does not specifically bind the monoclonal.

The optimal radioimmunoreactivity of the labeled monoclonal is determined in this system by varying the concentration of the imaging agent available for binding to the monoclonal antibody while keeping the concentration of the monoclonal antibody constant. The labeled monoclonals are then tested in the fixed cell immunoassay described above by adding the labeled monoclonal to the fixed cells at conditions of antigen excess. The labeled monoclonal giving the highest detectable binding is determined and can be used initially for in vivo radioimmunoimaging.

When an in vitro immunoassay is used to monitor the status of a cancer patient, a quantitative immunoassay procedure must be used. In such monitoring, assays are carried out periodically and the results compared to determine whether the patient's tumor burden has increased or decreased. Common assay techniques that may be used include direct and indirect assays. Direct assays involve incubating a tissue sample or cells from the patient with a labeled antibody. If the sample includes breast cancer cells, the labeled antibody will bind to those cells. After washing the tissue or cells to remove unbound labeled antibody, the tissue sample is read for the presence of labeled immune complexes. In indirect assays the tissue or cell sample is incubated with unlabeled monoclonal antibody. The sample is then treated with a labeled antibody against the monoclonal antibody (e.g., a labeled antimurine antibody), washed, and read for the presence of labeled ternary complexes.

For in vitro diagnostic use the antibodies will typically be distributed in kit form. These kits will typically comprise: the antibody in labeled or unlabeled form in suitable containers, reagents for the incubations and washings, a labeled antimurine antibody if the kit is for an indirect assay, and substrates or derivatizing agents depending on the nature of the label. For in vivo imaging use the antibody will also be distributed in kit form and will typically comprise the same types of components as mentioned above. The antibody may be supplied derivatized with an agent already bound to or chelated with the radioisotope to be used, or the monoclonal may be supplied derivatized with the binding or chelating agent only, and the radioisotope to be used may be supplied separately. The radioisotope to be used can be added just prior to use so that an optimal radioactivity level for imaging can be achieved at the time of administration of the radioimmunoimaging agent to the patient. Human breast cancer antigen controls and instructions may also be included if appropriate to the test.

The following examples provide a detailed description of the preparation, characterization, and use of representative monoclonal antibodies of this invention. These examples are not intended to limit the invention in any manner.

IMMUNIZATION

Fresh postsurgical human breast cancer tissue and a variety of normal tissues were used to prepare membrane extracts by homogenization and discontinuous sucrose gradient centrifugation. Human breast cancer cell lines were obtained from the Breast Cancer Task Force, the American Type Culture Collection (ATCC), and from Dr. Jorgen Fogh at Memorial Sloan Kettering. The cells were maintained and passaged as recommended by the Breast Cancer Task Force, the ATCC and Dr. Fogh. For immunizations, either membrane extract containing 100 µg of protein (Lowry assay) or ten million live breast cancer cells were inoculated intra-peritoneally into five week old Balb/c mice. The mice were boosted identically twice at monthly intervals. Three days after the last boost, the spleens were removed for cell fusion.

HYBRIDOMA METHODS

Somatic cell hybrids were prepared by the method of Buck, D. W., et al, supra, using the murine myeloma line Sp-2/0/Ag14. All hybrodima cell lines were cloned by limiting dilution. Half of the fusions employed splenocytes from mice immunized with breast cancer membrane extracts and half used splenocytes from mice immunized with live breast cancer cell lines. Eighty-three thousand four hundred twenty-four wells were generated from those fusions, of which 22,459 exhibited hybridoma growth.

SCREENING METHODS

Hybridoma supernatant was assayed for reactive antibody in either a solid phase enzyme-linked immunosorbent assay (ELISA) with the immunizing breast cancer membrane extract or an indirect immunofluorescence assay with the immunizing breast cancer cell line. For the solid phase membrane ELISA, 40 µl of 0.1 mg/ml breast cancer membrane protein were placed in polyvinyl chloride (PVC) microtiter wells for 12 hours at 4° C. The extract was aspirated and the wells washed with phosphate buffered saline (PBS) containing 1% bovine serum albumin (BSA). The wells were then incubated with 45 µl of a 1:10 dilution of hybridoma supernatant. The diluent was media with 25 mM of a buffer, 10% bovine serum, and 0.1% sodium azide. After 30 minutes at room temperature, the wells were again washed and incubated 45 minutes at 37° C. with a 1:200 dilution of peroxidase conjugated goat anti-mouse IgG. The diluent was PBS. The wells were then washed with PBS and reacted with 200 µl of 1,2-azino-di(3-ethylbenzthiazoline sulphonic acid) in 0.1M sodium citrate buffer pH 4.2 for 30 minutes at room temperature. Optical density was measured at 405 nm on a MicroElisa Reader. For each experiment a positive control, anti-beta 2 microglobulin at 5 µg/ml, was reacted with normal human kidney membrane. This gave an optical density of 1.0±0.1 (standard deviation). The background was 0±0.1 optical density units (O.D.) using media without mouse monoclonal antibody. Wells that gave a reaction on the breast cancer membrane extract of greater than 0.7 O.D. were saved.

For the indirect immunofluorescence cell line assay 100,000 breast cancer cells of the immunizing cell line were placed overnight with appropriate media in each chamber of a set of eight chambered slides. Similarly, 100,000 fibroblast cells from cell line CC95 were incubated overnight in chambered slide wells. The cells were washed with PBS containing 1% BSA. The wells, both breast cancer and fibroblast, were incubated for 30 minutes at 4° C. with 1:10 dilutions of hybridoma supernatant. The cells were again washed and incubated 30 minutes at 4° C. with a 1:50 dilution of fluorescein isothiocyanate (FITC)-conjugated goat F(ab')2 anti-mouse Ig. The cells were washed three times, fixed in 1.5% formaldehyde in PBS for five minutes, chambers removed and rinsed in PBS. The slides were then mounted in a composition containing polyvinyl alcohol, glycerol, buffers and a preservative and examined with a fluorescence microscope. Hybridoma wells showing strong fluorescent binding to the breast cancer cells but no fluorescent binding to fibroblasts were saved. Five thousand one hundred fifty-six hybridoma wells revealed breast cancer reactivity in the initial screen.

Supernatants from the 5156 positive wells were then tested in solid phase ELISA with seven normal tissue membrane extracts (liver, lung, colon, stomach, kidney, tonsil, and spleen). Any well supernatant giving an ELISA O.D. greater than 0.3 was discarded. One thousand one hundred one of the supernatants were found to be unreactive with the normal tissue extracts.

The 1101 hybridoma supernatants were tested on frozen sections of human breast carcinoma tissues. Six micron sections were attached to slides, fixed 10 minutes in acetone at 4° C., dried 10 minutes at room temperature, washed with PBS, blocked with horse serum and incubated 20 minutes at room temperature with 100 μl neat hybridoma supernatant. The slides were washed with PBS, and finally incubated 20 minutes at 37° C. with a 1:50 dilution of peroxidase conjugated rabbit anti-mouse Ig, washed again with PBS, and finally incubated 7.5 minutes at 37° C. with 0.5 mg/ml diaminobenzidine in 0.05M Tris buffer pH 7.2 containing 0.01% hydrogen peroxide. The slides were stained with hematoxylin, dehydrated and mounted in a medium containing 35.9% methyl/n-butylmethacrylate copolymer, 7.1% butyl benzyl phthalate, and 0.3% 2,6-ditertbutyl-p-cresol. One hundred twenty-four wells yielded breast cancer selective binding and were cloned.

PURIFICATION AND CLASS DETERMINATION

Immunoglobulin class and subclass of the monoclonal breast cancer selective antibodies were determined by an immunodot assay essentially the same as that described in McDougal et al. *J. Immunol. Meth.* 63: 281–290 (1983). Antibodies were also internally labeled by growing 2–3×10$^6$ hybridoma cells for four hours in methionine-free medium containing 0.2 μCi $^{35}$S methionine. $^{35}$S-labeled antibodies were immunoprecipitated with fixed staphylococcus A cells, or with fixed staphylococcus A cells precoated with rabbit anti-mouse immunoglobulin, and the immunoprecipitates were analyzed by SDS-PAGE to determine antibody light and heavy chain mobility, lack of extra chains, and the ability of each antibody to bind staphylococcal protein A.

The antibodies were expanded in vivo. Balb/c or F1 (C57B/6×Balb/c) mice were primed with 0.5 ml pristane intraperitoneally (ip) and after 10–14 days inoculated with one million log phase hybridoma cells in PBS. Ascites fluid was stored at −70° C. and thawed and filtered through a 0.8 micron filter unit before further purification.

Some IgG antibodies that bound staphylococcal protein A were purified by affinity chromatography on protein A-chromatographic resin containing either agarose, dextran and/or acrylamide with pH step gradient elution. IgG antibodies that did not bind protein A were precipitated by addition of ammonium sulfate to 40% saturation at 0° C. or by binding to DEAE or affigel ™ (Biorad, Richmond, Calif.). Alternatively, IgG antibodies are purified by chromatography using a Sephacryl S-200 column, followed by DEAE cellulose as described. The precipitates were redissolved in PBS, dialysed to 20 mM Tris pH 7.2 and chromatographed on a 1.6×50 cm column of diethylaminoethyl cellulose (DEAE) eluting with a 1.5 liter 0–600 mM NaCl gradient at 4° C. at a flow rate of 1 ml/min. In each case, column fractions were monitored by SDS-PAGE and the purest antibody fractions were pooled, concentrated to 1–3 mg/ml, dialysed to PBS/0.02% NaN$_3$, and stored at 4° C.

IgM antibodies were purified by gel filtration material on a 2.6×40 cm column of Sephacryl S-300 or other gel filtration or resin containing agarose, dextran and/or acrylamide, eluting with PBS/0.01% sodium azide at room temperature at a flow rate of 1 ml/min.

SELECTIVITY DETERMINATION

In order to evaluate their selectivity for breast cancer, the purified antibodies were tested by immunoperoxidase section staining on sections of sixteen normal tissues, and by immunofluorescent cell sorting on five blood cell types. Immunoperoxidase staining was performed as above except that known dilutions of purified antibodies in PBS in the range of 1–40 μg/ml were used instead of hybridoma supernatants. The pure antibodies were first titrated to find the minimal concentration giving strong immunoperoxidase staining on breast cancer sections and then used at the concentration for the normal tissue tests. Peripheral bood cells (platelets, lymphocytes, red blood cells, granulocytes, and monocytes) were prepared by centrifugation using a medium which separates monocytes from polymorphonuclear leucocytes. The cells were reacted with antibody at the optimal concentration determined above for 30 minutes at 4° C., washed, reacted with a 1:50 dilution of fluorescein isothiocyanate-conjugated goat anti-mouse Ig for 30 minutes at 4° C., washed again and examined in a cell sorter. The wash buffer and diluents were PBS with 1% gelatin and 0.02% sodium azide. The cell sorter was equipped with a 76 micron nozzle and a one watt argon ion laser at 488 nm. An 80 mm confocal lens was used on the optical rail assembly for focusing. Other filters used were a 515 nm interference filter and a 515 nm absorbance filter (for scattered laser light) and a neutral density 1.5 filter for forward angle light scatter. Contour plots of log fluorescein fluorescence versus forward angle light scatter were used for sample analysis. No blood cell types showed detectable binding.

The binding behaviors of the claimed antibodies are reported in Table I below. The following abbreviations are used to denote structures bound by the antibodies: Ac, acini; G, glands; T, tubules; D, ducts; L, lumen; W, seat glands; E, epithelium; S, sebaceous glands; Gr, granulocytes; Mk, megakaryocytes; M, macrophage; Ly, lymphocytes; Bl, Basal layer; Fe, focal epithelium; A, alveolar lining cells; B, Bowman's capsule; Mu, muscle; and I, islets; H, hair follicles; U, glomeruli; and V, vessels/endothelial.

TABLE 1

| | | | | | | | | |
|---|---|---|---|---|---|---|---|---|
| Normal Tissue Bindings of Imaging MABS | | | | | | | | |
| MAB | Pancreas | Esophagus | Lung | Kidney | Colon | Stomach | Brain | Tonsil |
| 2G3 | 2Ac | 2E | 1A | 2T | P | 1L | 0 | 1E |
| 9C6 | 0 | 2E | 0 | 0 | 0 | 1L | 0 | 1Ly, 2E |
| 32A1 | 1D | 1E | 1A, M | 1T, U | 0 | 0 | 1My | 0 |
| 33F8 | 0 | 2E | 0 | 1T | 0 | 0 | 0 | 1Ly |
| 35E10 | 0 | 2E | 1A, 1M | 0 | 0 | 1G | 0 | 1Ly |
| 41B4 | 0 | 0 | 0 | 0 | 0 | 0 | 0 | 1E |
| 87H7 | 1D | 1E | 0 | 0 | 1G | 1G | 0 | 1Ly, E |
| 106A10 | 1Ac, D | 1E | 1M | 0 | 0 | 0 | 0 | 2E |
| 113F1 | 2Ac | 2E | 0 | 0 | 0 | 2G | 0 | 1E |
| 120H7 | 0 | 1E | 0 | 1T | 0 | 1L | 0 | 0 |

TABLE 1-continued

Normal Tissue Bindings of Imaging MABS

| MAB | | | | | | | | |
|---|---|---|---|---|---|---|---|---|
| 140A7 | 1Ac, D | 0 | 0 | 2T, B | 0 | 0 | 1Ly | 2 |
| 200F9 | 1Ac | 0 | 0 | 2L | 0 | 0 | 0 | 0 |
| 203E2 | 2Ac | 1E | 2A | 2L | 0 | 0 | 0 | 0 |
| 219F3 | 1Ac | 2E | 0 | 1T | 0 | 0 | 0 | 1Ly, E |
| 245E7 | 1L | 0 | 1A, M | 0 | 0 | 2L | 0 | 1E |
| 254H9 | 2Ac | 2E | 1A | 2T | 0 | 1G | 0 | 0 |
| 260F9 | 1Ac | 2E | 0 | 1T | 0 | 1G | 0 | 2E |
| 266B2 | 1Ac, 1D | 2E | 0 | 1T | 0 | 0 | 0 | 2E |
| 317G5 | 1Ac, 1 | 0 | 0 | 2T | 1G | 0 | 0 | 0 |
| 369F10 | 0 | 0 | 0 | 0 | 0 | 1G | 0 | 0 |
| 387H9 | 1D | 0 | 0 | 0 | 0 | 0 | 0 | 1Ly, 1E |
| 421E8 | 1Ac | 1E | 0 | 1T | 0 | 1G | 0 | 0 |
| 451C3 | 0 | 0 | 2M | 0 | 0 | 0 | 1V | 2Ly, 1Bl |
| 452E12 | 0 | 0 | 0 | 0 | 0 | 0 | 0 | 0 |
| 452F2 | 0 | 0 | 0 | 0 | 0 | 0 | 0 | 0 |
| 454A12 | 0 | 0 | 1M | 0 | 1G | 0 | 0 | 0 |
| 454C11 | 1D | 1-2E | 0 | 1T | 0 | 0 | 0 | 1E |
| 457D7 | 0 | 0 | 0 | 0 | 0 | 1G | 0 | 0 |
| 520C9 | 0 | 0 | 0 | 1T | 0 | 0 | 0 | 0 |
| 650E2 | 1Ac, 1 | 0 | 1-2A | 2T | 2G | 0 | 0 | 0 |
| 697B3 | 0 | 0 | 0 | 2T | 0 | 0 | 0 | 0 |
| 741F8 | 0 | 0 | 0 | 0 | 0 | 0 | 0 | 0 |
| 759E3 | 0 | 0 | 0 | 0 | 0 | 0 | 0 | 1E |
| 788G6 | 0 | 0 | 0 | 2T | 0 | 0 | 0 | 1Fe |

| MAB | Liver | Heart | Ovary | Skin | Bone Marrow | Uterus | Bladder | Normal Breast |
|---|---|---|---|---|---|---|---|---|
| 2G3 | 0 | 0 | 0 | 0 | 0 | 2L | 2E | 2E |
| 9C6 | 0 | 0 | 0 | 0 | 2Gr | 0 | 0 | 2E |
| 32A1 | 0 | 0 | 0 | 1S, W | 0 | 1Mu | 0 | 0 |
| 33F8 | 0 | 0 | 0 | 1W | 1Mk | 1L | 1E | 0 |
| 35E10 | 0 | 0 | 0 | 2W | 2Gr | 0 | 0 | 0 |
| 41B4 | 0 | 0 | 0 | 1W | 0 | 0 | 0 | 1E |
| 87H7 | 2 | 0 | 0 | 2H | 0 | 0 | 0 | 1E |
| 106A10 | 2D | 0 | 0 | 2E, W | 0 | 1G | 2E | 2E |
| 113F1 | 0 | 0 | 0 | 0 | 0 | 0 | 1E | 0 |
| 120H7 | 0 | 0 | 0 | 2S | 0 | 2L | 0 | 0 |
| 140A7 | 0 | 0 | 2E, 1S | 0 | 0 | 0 | 0 | 0 |
| 200F9 | 0 | 0 | 0 | 2S | 0 | 0 | 0 | 0 |
| 203E2 | 0 | 0 | 0 | 2S | | | | 0 |
| 219F3 | 0 | 0 | 0 | 2H, W | 1-2Gr | 1G | 0 | 2E |
| 245E7 | 0 | 0 | 0 | 2S | 0 | 2L | 1E | 2L |
| 254H9 | 0 | 0 | 0 | 0 | | | | 2L |
| 260F9 | 2D | 0 | 0 | 2E, 2H | 0 | 1L | 2E | 2E |
| 266B2 | 0 | 0 | 0 | 2E, 2W | 0 | 0 | 1E | 1E |
| 317G5 | 2D | 0 | 0 | 0 | 0 | 1G | 0 | 0 |
| 369F10 | 0 | 0 | 0 | 1S | 0 | 0 | 0 | 0 |
| 387H9 | 1, 1D | 0 | 1V | 0 | 2 | 1G | 0 | 1 |
| 421E8 | 1 | 0 | 0 | 0 | 0 | 1G | 0 | 0 |
| 451C3 | 0 | 0 | 0 | 0 | 2 | 1G | 0 | 0 |
| 452E12 | 1 | 0 | 0 | 2S | 0 | 0 | 0 | 2 |
| 452F2 | 0 | 0 | 0 | 0 | 0 | 0 | 0 | 0 |
| 454A12 | 0 | 0 | 0 | 1E, H | 0 | 1G | 1E | 1E |
| 454C11 | 1D | 0 | 0 | 1E, H | 0 | 1G | 1E | 1E |
| 457D7 | 1 | 0 | 0 | 2S | 0 | 0 | 0 | 2 |
| 520C9 | 0 | 0 | 0 | 0 | 0 | 0 | 0 | 0 |
| 650E2 | 2D | 0 | 0 | 0 | 0 | 2G | 0 | 1 |
| 697B3 | 0 | 0 | 0 | 2S | 0 | 2L | 0 | 2L |
| 741F8 | 0 | 0 | 0 | 0 | 0 | 0 | 0 | 0 |
| 759E3 | 0 | 0 | 0 | 0 | 0 | 0 | 0 | 0 |
| 788G6 | 0 | 0 | 0 | 0 | 0 | 0 | 0 | 0 |

0 = No binding
1 = Moderate binding
2 = Strong binding

BREAST CANCER TUMOR BINDING RANGE DETERMINATION

In order to determine how wide a range of breast cancers might be recognized by each antibody, the anti-breast cancer selective antibodies were tested by immunoperoxidase staining on frozen section of 27 different breast tumors. The breast cancers used for section staining were all infiltrating intraductal carcinomas, so no correlation of antibody binding with histologic type of breast cancer could be made. In addition, no correlation between antibody binding and the nodal status or estrogen receptor status was found for the twelve tumors for which donor information was available. Antibodies reacted equally well with metastatic and primary breast tumors. The results of these tests for the claimed antibodies are reported in Table 2 below.

TABLE 2

BREAST TUMOR BINDING OF IMAGING MABS

| MAB | BCLA | BCKA | BCJA | BCIA | BCHA | BCGA | BCE | BCEA | BCTA | BCUA | BCRA | BCSA | BCO | BCA | BCMA |
|---|---|---|---|---|---|---|---|---|---|---|---|---|---|---|---|

TABLE 2-continued

BREAST TUMOR BINDING OF IMAGING MABS

| MAB | | | | | | | | | | | | | | | |
|---|---|---|---|---|---|---|---|---|---|---|---|---|---|---|---|
| 2G3 | 1 | 2 | 1 | 2 | 2 | 2 |  | 2 | 2 | 2 | 2 | 2 | 2 | 2 | 1 |
| 9C6 | 2 | 2 | 2 | 2 | 2 | 2 | 0 | 1 | 0 | 2 | 1 | 0 | 2 | 1 | 2 |
| 32A1 | 1 | 1 | 0 | 1 | 0 | 0 | 0 | 0 | 0 | 1 | 0 | 1 | 0 | 0 | 0 |
| 33F8 | 1 | 1 | 0 | 0 | 0 | 0 | 1 | 0 | 0 | 0 | 0 | 0 | 1 | 0 | 0 |
| 35E10 | 2 | 2 | 0 | 2 | 0 | 2 | 2 | 0 | 0 | 2 | 2 | 2 | 2 | 2 | 0 |
| 41B4 | 2 | 1 | 1 | 2 | 0 | 0 | 1 | 1 | 0 | 0 | 1 | 0 | 0 | 1 | 2 |
| 87H7 | 2 | 2 | 2 | 2 | 2 | 1 | 1 | 2 | 0 | 1 | 2 | 2 | 1 | 1 | 2 |
| 106A10 | 1 | 1 | 1 | 1 | 1 | 1 | 1 | 0 | 0 | 1 | 1 | 1 | 2 | 1 | 0 |
| 113F1 | 0 | 1 | 1 | 0 | 0 | 0 | 0 | 0 | 0 | 0 | 1 | 0 | 0 | 0 | 0 |
| 120H7 | 2 | 2 | 0 | 2 | 0 | 0 | 0 | 2 | 2 | 0 | 1 | 1 | 2 | 0 | 2 |
| 140A7 | 0 | 0 | 1 | 1 | 2 | 0 | 2 | 0 | 2 | 2 | 2 | 2 | 1 | 2 | 0 |
| 200F9 | 0 | 2 | 0 | 2 | 0 | 2 | 2 | 0 | 0 | 0 | 0 | 2 | 2 | 0 | 0 |
| 203E2 | | | | | | | | | | | | | | | |
| 219F3 | 2 | 2 | 2 | 2 | 2 | 1 | 0 | 1 | 1 | 2 | 0 | 0 | 2 | 1 | 2 |
| 245E7 | 2 | 2 | 2 | 2 | 2 | 2 | 2 | 2 | 2 | 2 | 2 | 2 | 2 | 2 | 2 |
| 254H9 | | | | | | | | | | | | | | | |
| 260F9 | 0 | 1 | 0 | 1 | 0 | 1 | | 1 | 2 | 0 | 0 | 0 | 1 | 0 | 0 |
| 266B2 | 1 | 2 | 0 | 1 | 0 | 1 | | 0 | 2 | 1 | 1 | 0 | 1 | 0 | 1 |
| 317G5 | 1 | | 0 | 0 | 1 | | | 0 | 0 | 0 | 1 | 1 | | 0 | 1 |
| 369F10 | 2 | 2 | 2 | 2 | 0 | 1 | | 1 | 0 | 1 | 1 | 2 | 2 | 0 | 0 |
| 387H9 | 0 | | 1 | 1 | 0 | | | 0 | 0 | 0 | 1 | 0 | | 0 | 0 |
| 421E8 | 1 | | 1 | | 1 | | | 0 | 1 | 1 | 1 | 1 | | | 1 |
| 451C3 | 0 | 0 | 1 | 0 | 1 | 0 | | 0 | 2 | 1 | 0 | 0 | | 0 | 1 |
| 452E12 | 1 | 0 | 0 | 2 | 0 | 0 | | 0 | 0 | 0 | 2 | 0 | | 1 | 2 |
| 452F2 | 0 | 2 | 0 | 2 | 0 | 0 | | 1 | 0 | 1 | 0 | 0 | | 0 | 1 |
| 454A12 | 1 | 1 | 0 | 2 | 1 | 0 | | 0 | 0 | 2 | 0 | 0 | | 0 | 0 |
| 454C11 | 1 | 2 | 0 | 2 | 1 | 1 | | 2 | 1 | 1 | 0 | 0 | | 1 | 2 |
| 457D7 | 1 | | 0 | 1 | 0 | | | 0 | 0 | 0 | 1 | 0 | | 1 | 2 |
| 520C9 | 0 | | 0 | 2 | 0 | | | 2 | 0 | 1 | 0 | 0 | | 0 | 2 |
| 650E2 | 1 | | 1 | | 1 | | | 0 | 0 | 1 | 1 | 1 | | | 2 |
| 697B3 | 0 | 2 | 2 | 0 | | | | 1 | 2 | 1 | 2 | 2 | | 1 | 0 |
| 741F8 | 0 | 0 | 2 | 0 | | | | 2 | 0 | 1 | 0 | 0 | 0 | 0 | 2 |
| 759E3 | 0 | | 0 | 0 | | | | 2 | 0 | 2 | 0 | 0 | | | 2 |
| 788G6 | 2 | 2 | | 0 | | | | 0 | 0 | 0 | 0 | 2 | | | 0 |

| MAB | BCBA | BCNA | BCFA | LMA | LME | MBA | BCZ | BCYA | BCKB | BCGB | BCIC | BCEC |
|---|---|---|---|---|---|---|---|---|---|---|---|---|
| 2G3 | 2 | 2 | 2 | 2 | 2 | 2 | 2 | | | | | |
| 9C6 | 1 | 1 | 2 | 2 | 2 | 2 | | | | | | |
| 32A1 | 0 | 0 | 1 | 1 | 0 | 0 | | | | | | |
| 33F8 | 0 | 0 | 0 | 0 | 0 | 0 | | | | | | |
| 35E10 | 2 | 2 | 0 | 0 | 2 | 0 | | | | | | |
| 41B4 | 1 | 0 | 2 | 2 | 2 | 1 | | | | | | |
| 87H7 | 1 | 2 | 2 | 2 | 2 | 2 | | | | | | |
| 106A10 | 1 | 2 | 1 | 1 | 1 | 1 | | | | | | |
| 113F1 | 0 | 0 | 0 | 0 | 0 | 0 | | | | | | |
| 120H7 | 2 | 2 | 2 | 2 | 0 | 2 | | | | | | |
| 140A7 | 2 | 2 | 2 | 2 | 0 | 2 | | | | | | |
| 200F9 | 0 | 2 | 2 | 2 | 2 | 1 | | | | | | |
| 203E2 | | | | | | | | | | | | |
| 219F3 | 1 | 1 | 2 | 2 | 2 | 2 | | | | | | |
| 245E7 | 2 | 2 | 2 | 2 | 2 | 2 | | | | | | |
| 254H9 | | | | | | | | | | | | |
| 266F9 | 1 | 1 | 1 | 0 | 1 | 1 | 0 | | | | | |
| 266B2 | 1 | 2 | 1 | 0 | 1 | 1 | 1 | | | | | |
| 317G5 | 0 | 1 | 1 | 0 | 0 | 0 | 0 | 0 | 1 | 1 | | |
| 369F10 | 2 | 2 | 2 | 2 | 2 | 2 | 1 | | | | | |
| 387H9 | 1 | 0 | 1 | 0 | 0 | 0 | 0 | 0 | 0 | 1 | | |
| 421E8 | 1 | 1 | 1 | 1 | 0 | 1 | 1 | 1 | 1 | 0 | 1 | 0 |
| 451C3 | 0 | 1 | 0 | 1 | 0 | 1 | 0 | 0 | | | | |
| 452E12 | 0 | 1 | 0 | 1 | 1 | 1 | 1 | 1 | | | | |
| 452F2 | 0 | 0 | 0 | 0 | 0 | 0 | 0 | 0 | | | | |
| 454A12 | 0 | 1 | 0 | 0 | 0 | 0 | 0 | 0 | | | | |
| 454C11 | 0 | 1 | 1 | 0 | 1 | 1 | 1 | 2 | | | | |
| 457D7 | 0 | 1 | 1 | 1 | 0 | 1 | 1 | 1 | 0 | | | |
| 520C9 | 0 | 1 | 0 | 0 | 0 | 0 | 0 | 0 | 0 | | | |
| 650E2 | 1 | 2 | 1 | 1 | 0 | 1 | 1 | 1 | 2 | 1 | 2 | 2 |
| 697B3 | 2 | 2 | 2 | 0 | 2 | 2 | 2 | 1 | 2 | 2 | | |
| 741F8 | 0 | 0 | 0 | 0 | 0 | 0 | 0 | 0 | 0 | | | |
| 759E3 | 0 | 0 | 0 | 0 | 0 | 0 | 0 | 0 | 0 | 0 | | 0 |
| 788G6 | 0 | 2 | 2 | 2 | 2 | 2 | 2 | 2 | 0 | 2 | 2 | 2 |

BREAST CANCER CELL BINDING RANGE DETERMINATION

Antibodies were further evaluated for range of breast cancer cell line recognition by immunofluorescence assays on 14 breast cancer cell lines. Table 3 below reports the results of these tests for the claimed antibodies.

TABLE 3

Breast Cancer Cell Line Binding of Imaging MABS

| MAB | MCF7 | BT20 | ZR751 | MDA-MB231 | CAMA1 | ALAB | BT549 | BT474 | T47D | MDA-MB157 | MB330 | MDA-SKBR3 | MDA-BT483 | ZR7530 |
|---|---|---|---|---|---|---|---|---|---|---|---|---|---|---|
| 2G3 | 4 | 3 | 3 | 2 | 4 | 2 | 4 | 2 | 3 | 2 | | 3 | 4 | 3 |
| 9C6 | 3 | 0 | 3 | 0 | 4 | 2 | 0 | 3 | 3 | 0 | 0 | 2 | 0 | 2 |
| 32A1 | 3 | 2 | 2 | 2 | 2 | 2 | 0 | 3 | 3 | 2 | 0 | 2 | 1 | 3 |
| 33F8 | 2 | 3 | 2 | 0 | 2 | 3 | 2 | 2 | 0 | 3 | 2 | 2 | 0 | 1 |
| 35E10 | 1 | 0 | 0 | 0 | 0 | 0 | 0 | 2 | 0 | 0 | 0 | 0 | 0 | 2 |
| 41B4 | 1 | 0 | 0 | 0 | 0 | 0 | 0 | 0 | 1 | 0 | 0 | 0 | 0 | 0 |
| 87H7 | 0 | 0 | 1 | 1 | 0 | 0 | 0 | | 0 | 0 | 0 | 1 | 0 | 0 |
| 106A10 | 3 | 3 | 2 | 2 | 2 | 0 | 0 | 2 | 3 | 2 | 2 | 3 | 2 | 2 |
| 113F1 | 3 | 4 | 2 | 2 | 4 | 0 | 0 | 4 | 3 | 3 | 2 | 4 | 2 | 0 |
| 120H7 | 3 | 2 | 3 | 0 | 3 | 0 | 2 | 0 | 0 | 0 | 0 | 2 | 3 | 2 |
| 140A7 | 3 | 2 | 1 | 0 | 2 | 0 | 1 | 0 | 0 | 0 | 3 | 0 | 2 | 1 |
| 200F9 | 3 | 3 | 2 | 0 | 2 | 2 | 3 | 0 | 3 | 2 | 0 | 0 | 3 | 2 |
| 203E2 | 4 | 4 | 3 | 0 | 4 | 2 | 4 | 2 | 4 | 3 | 0 | 2 | 4 | 3 |
| 219F3 | 3 | 3 | 4 | 0 | 4 | 3 | 2 | 3 | 3 | 4 | 0 | 3 | 2 | 3 |
| 245E7 | 4 | 4 | 4 | 2 | 4 | 2 | 4 | 2 | 4 | 4 | | 3 | 4 | 4 |
| 254H9 | 4 | 4 | 4 | 2 | 4 | 1 | 3 | 2 | 4 | 4 | | 2 | 3 | 3 |
| 260F9 | 3 | 3 | 3 | 2 | 3 | 2 | 0 | 2 | 2 | 2 | ND | 4 | 2 | 3 |
| 266B2 | 3 | 2 | 2 | 2 | 3 | 0 | 0 | | 2 | 2 | | 2 | 2 | 2 |
| 317G5 | 2 | 3 | 3 | 0 | 4 | 3 | 1 | | 3 | 4 | 0 | 3 | 2 | 3 |
| 369F10 | 1 | 0 | 0 | 0 | 2 | 0 | 0 | | 0 | 0 | | 0 | 2 | 0 |
| 387H9 | 3 | 2 | 2 | | 3 | 3 | 0 | | 2 | 2 | | 2 | 2 | 2 |
| 421E8 | 2 | | 2 | | 2 | | 0 | | | | | 0 | 2 | 0 |
| 451C3 | 3 | 2 | 2 | | 2 | 2 | 2 | | 4 | 2 | | 2 | 0 | 2 |
| 452E12 | 0 | 0 | 0 | | 0 | 0 | 0 | | 0 | 0 | | 0 | 0 | 0 |
| 452F2 | 0 | 1 | 2 | | 2 | 2 | 0 | | 1 | 0 | | 3 | 2 | 3 |
| 454A12 | 2 | 2 | 2 | | 2 | 3 | 2 | | 3 | 2 | | 2 | 2 | 2 |
| 454C11 | 2 | 2 | 2 | 2 | 2 | 2 | 1 | | 1 | 0 | | 4 | 2 | 4 |
| 457D7 | 0 | 0 | 0 | | 1 | | 0 | | 0 | 0 | | 0 | 2 | 0 |
| 520C9 | 1 | 0 | 1 | | 2 | | 0 | | 1 | 0 | | 3 | 2 | 2 |
| 650E2 | 3 | 2 | 3 | | 3 | | 0 | | 3 | 3 | | 3 | 2 | 3 |
| 697B3 | 2 | | | | 4 | | 3 | | 4 | 3 | | 0 | 4 | 2 |
| 741F8 | 1 | | | | 2 | | 0 | | 2 | 0 | | 4 | 2 | 2 |
| 759E3 | 0 | | | | 2 | | | | 2 | | | 3 | 0 | 4 |
| 788G6 | 2 | | | | 2 | | | | 3 | | | 0 | 3 | 2 |

0 = Negative
1 = Weak
2 = Moderate
3 = Strong
4 = Very strong

NON-BREAST CANCER BINDING OF IMAGING MONOCLONAL ANTIBODIES

Finally, the antibodies were tested by immunoperoxidase staining on eleven non-breast malignancies. The results for the claimed antibodies are reported in Table 4 below.

TABLE 4

Nonbreast Cancer Bindings of Imaging MABs

| MAB | Colon | Lung | Prostate | Pancreas | Uterus | Lymphoma | Stomach | Bladder | Esophagus | Melanoma | Ovarian |
|---|---|---|---|---|---|---|---|---|---|---|---|
| 2G3 | 2 | 0 | 2 | 0 | 2 | 0 | 2 | 0 | 0 | 0 | 2 |
| 9C6 | 1 | 0 | 0 | 0 | 2 | 1 | 0 | 0 | 0 | 0 | 1 |
| 32A1 | 0 | 0 | 0 | 2 | 0 | 0 | 1 | 0 | 0 | 0 | 0 |
| 33F8 | 0 | 1 | 0 | 0 | 1 | 0 | 0 | 0 | 0 | 0 | 1 |
| 35E10 | 2 | 2 | 1 | 2 | 0 | 2 | 0 | 0 | 0 | 0 | 0 |
| 41B4 | 0 | 0 | 2 | 0 | 0 | 0 | 0 | 0 | 0 | 0 | 0 |
| 87H7 | 0 | 1 | 2 | 0 | 1 | 0 | 0 | 2 | 1 | 0 | 0 |
| 106A10 | 0 | 1 | 1 | 0 | 1 | 1 | 1 | 0 | 1 | 0 | 0 |
| 113F1 | 0 | 2 | 0 | 2 | 1 | 2 | 2 | 0 | 1 | 0 | 0 |
| 120H7 | 0 | 0 | 2 | 0 | 1 | 1 | 0 | 0 | 0 | 0 | 2 |
| 140A7 | 0 | 0 | 0 | 1 | 2 | 1 | 2 | 1 | 0 | 0 | 0 |
| 200F9 | 0 | 1 | 0 | 0 | 0 | 0 | 0 | 0 | 0 | 0 | 1 |
| 203E2 | | | | | | | | | | | |
| 219F3 | 0 | 0 | 1 | 0 | 1 | 1 | 0 | 0 | 0 | 0 | 1 |
| 245E7 | 0 | 2 | 2 | 2 | 2 | 2 | 0 | 0 | 0 | 0 | 2 |
| 254H9 | | | | | | | | | | | |
| 260F9 | 0 | 0 | 1 | 1 | 1 | 0 | 0 | 0 | 1 | 0 | 2 |
| 266B2 | 0 | 1 | 1 | 1 | 1 | 0 | 1 | 0 | 1 | 0 | 1 |
| 317G5 | 1 | 1 | 0 | 0 | 0 | 0 | 0 | 0 | 0 | 0 | 1 |
| 369F10 | 0 | 1 | 1 | 1 | 0 | 0 | 0 | 0 | 0 | 0 | 2 |
| 387H9 | | | | | | | | | | | |
| 421E8 | 1 | 1 | 1 | 1 | 1 | 0 | 0 | 0 | 1 | 1 | 1 |
| 451C3 | 1 | 1 | 1 | 1 | 2 | 1 | 2 | 1 | 2 | 1 | 1 |
| 452E12 | 0 | 0 | 1 | 0 | 1 | 0 | 0 | 0 | 1 | 0 | 0 |
| 452F2 | 0 | 0 | 0 | 0 | 0 | 0 | 0 | 0 | 0 | 0 | 0 |
| 454A12 | 0 | 0 | 0 | 1 | 2 | 0 | 1 | 1 | 2 | 2 | 1 |
| 454C11 | 0 | 0 | 1 | 1 | 2 | 0 | 0 | 0 | 0 | 0 | 1 |

TABLE 4-continued

| | Nonbreast Cancer Bindings of Imaging MABs | | | | | | | | | | |
|---|---|---|---|---|---|---|---|---|---|---|---|
| MAB | Colon | Lung | Prostate | Pancreas | Uterus | Lymphoma | Stomach | Bladder | Esophagus | Melanoma | Ovarian |
| 457D7 | 0 | 0 | 1 | 0 | 0 | 0 | 0 | 0 | 0 | 0 | 0 |
| 520C9 | 0 | 1 | 1 | 1 | 1 | 0 | 0 | 0 | 0 | 0 | 0 |
| 650E2 | 2 | 2 | 2 | 2 | 2 | 0 | 0 | 0 | 0 | 0 | 2 |
| 697B3 | 0 | 0 | 0 | 0 | 0 | 0 | 0 | 0 | 0 | 0 | 0 |
| 741F8 | 0 | 0 | 0 | 0 | 0 | 0 | 0 | 0 | 0 | 0 | 0 |
| 759E3 | 0 | 1 | 1 | 1 | 0 | 0 | 0 | 0 | 0 | 0 | 0 |
| 788G6 | 0 | 2 | 0 | 0 | 0 | 0 | 0 | 0 | 0 | 0 | 2 |

The tumor breast cancer range, breast cancer cell binding range, blood cell binding and selectivity characteristics for the monoclonal antibodies according to the invention are summarized in Table 5.

TABLE 5

| | Imaging MAB Candidates | | | |
|---|---|---|---|---|
| MAB | Blood Cells | Tumor Range | Cell Range | Selectivity |
| 2G3 | 0 | 1.00 | 1.00 | 0.078 |
| 9C6 | 0 | 0.86 | 0.57 | 0.063 |
| 32A1 | 0 | 0.33 | 0.79 | 0.078 |
| 33F8 | 0 | 0.19 | 0.71 | 0.063 |
| 35E10 | 0 | 0.62 | 0.14 | 0.070 |
| 41B4 | 0 | 0.67 | 0.00 | 0.023 |
| 87H7 | 0 | 0.95 | 0.00 | 0.078 |
| 106A10 | 0 | 0.86 | 0.86 | 0.086 |
| 113F1 | 0 | 0.14 | 0.79 | 0.047 |
| 120H7 | 0 | 0.67 | 0.57 | 0.047 |
| 140A7 | 0 | 0.71 | 0.36 | 0.070 |
| 200F9 | 0 | 0.52 | 0.71 | 0.031 |
| 203E2 | 0 | | 0.86 | 0.055 |
| 219F3 | 0 | 0.86 | 0.86 | 0.086 |
| 245E7 | 0 | 1.00 | 1.00 | 0.070 |
| 254H9 | 0 | | 0.92 | 0.064 |
| 260F9 | 0 | 0.52 | 0.92 | 0.089 |
| 266B2 | 0 | 0.71 | 0.83 | 0.070 |
| 317G5 | 0 | 0.43 | 0.77 | 0.055 |
| 369F10 | 0 | 0.81 | 0.17 | 0.023 |
| 389H9 | 0 | 0.29 | 0.91 | 0.086 |
| 421E8 | 0 | 0.81 | 0.57 | 0.055 |
| 451C3 | 0 | 0.38 | 0.91 | 0.070 |
| 452E12 | 0 | 0.52 | 0.00 | 0.023 |
| 452F2 | 0 | 0.24 | 0.55 | 0.000 |
| 454A12 | 0 | 0.29 | 1.00 | 0.031 |
| 454C11 | 0 | 0.76 | 0.75 | 0.078 |
| 457D7 | 0 | 0.55 | 0.10 | 0.039 |
| 520C9 | 0 | 0.25 | 0.40 | 0.008 |
| 650E2 | 0 | 0.86 | 0.90 | 0.008 |
| 697B3 | 0 | 0.81 | 0.88 | 0.070 |
| 741F8 | 0 | 0.18 | 0.63 | 0.000 |
| 759E3 | 0 | 0.14 | 0.78 | 0.008 |
| 788G6 | 0 | 0.62 | 0.83 | 0.016 |

ANTIBODY AFFINITY AND ANTIGEN DENSITY

Several of the claimed antibodies were iodinated and tested for binding to MCF-7, CAMA1, SKBR3 or ZR7530 cells. The antibodies were labeled with $^{125}I$ using chloramine T to a specific activity of approximately 10 $\mu Ci/\mu g$. To determine immunoradiochemical purity, 100,000 cpm of two of the labeled antibodies in 0.5 ml fetal calf serum was serially absorbed with five aliquots of target cells for 15 minutes at 0° C. (generally 4,000,000 cells per aliquot), and the remaining radioactivity in the supernatant after each absorption was determined.

For measurements of association constants known concentrations of labeled and unlabeled monoclonal antibodies were incubated with target cells in fetal calf serum for 15 minutes in ice. Aliquots of the cell/antibody mix were then counted in a gamma counter or filtered through Microfold filter plates (V & P Scientific) and the filters counted. To account for unbound antibody retained in liquid on the filters, controls containing the same concentrations of antibody but no cells were done in parallel. Association constants and antigen copy number per target are calculated from the affinity test results and are reported in Table 6 below.

TABLE 6

| Affinity and Antigen Copy Number of Imaging MABs | | | | |
|---|---|---|---|---|
| MAB | s | n | Ka | Cell Line |
| 2G3 | | 3700000 | $9.1 \times 10^6$ | MCF7 |
| 9C6 | | | | |
| 32A1 | | | | |
| 33F8 | | | | |
| 335E10 | | | | |
| 41B4 | | | | |
| 87H7 | | | | |
| 106A10 | | | | |
| 113F1 | | 2300000 | $1.1 \times 10^9$ | MCF7 |
| 120H7 | | 210000 | $6.2 \times 10^6$ | MCF7 |
| 140A7 | | | | |
| 200F9 | | | | |
| 203E2 | | | | |
| 219F3 | | | | |
| 245E7 | | | | |
| 254H9 | | | | |
| 260F9 | | 30000 | $6.0 \times 10^7$ | MCF7 |
| 266B2 | | 80000 | $2.7 \times 10^8$ | MCF7 |
| 317G5 | | 3200000 | $1.6 \times 10^6$ | CAMA1 |
| 369F10 | | | | |
| 387H9 | | | | |
| 421E8 | | | | |
| 451C3 | | 400000 | $1.4 \times 10^8$ | MCF7 |
| 452E12 | | | | |
| 452F2 | | 250000 | $6.8 \times 10^6$ | SKBR3 |
| 454A12 | | 470000 | $1.2 \times 10^8$ | MCF7 |
| 454C11 | | 390000 | $4.8 \times 10^7$ | ZR7530 |
| 457D7 | | | | |
| 520C9 | | 500000 | $8.2 \times 10^6$ | SKBR3 |
| 650E2 | | | | |
| 697B3 | | | | |
| 741F8 | | | | |
| 759E3 | | | | |
| 788G6 | | | | |

In order to identify the antigens recognized by the monoclonal antibodies according to the invention, immunoprecipitation of the antigens was carried out according to the following method. Eight mm diameter polystyrene balls (Precision Plastic Ball Co.) were covered with 10% fuming nitric acid in glacial acetic acid and were incubated for three hours in a 50° C. water bath. Following the acid treatment, the balls were rinsed three times with distilled water, covered with 1% sodium dithionite in 0.1M NaOH and incubated three hours in a 50° C. water bath. The balls were again rinsed three times with distilled water, covered with 0.1% 1-ethyl-3-(3-dimethylaminopropyl)-carbodiimide (EDAC), 0.2% suberic acid (suberic acid dissolved in dimethylfomamide) and incubated overnight at room temperature. The balls were rinsed three times with distilled water, and marked for identification.

Purified monoclonal antibodies were diluted 0.2 mg/ml in 2-(N-morpholino)ethane sulfonic acid buffer, and the previously treated and marked polystyrene balls were placed in individual tubes and covered with 450 microliters diluted antibody and 50 microliters of fresh 1% EDAC. Tubes were capped and incubated at 25° C. for 24 hours. Following this incubation, the balls were rinsed twice with PBS and were either used fresh or were stored for several days at 4° C. before use.

Freshly labeled target cell extracts were prepared from human breast cancer cell lines labeled with 125-I by the lactoperoxidase method of Marchalonis, J., "An Enzymic Method for the Trace Iodination of Immunoglobulins and other Proteins", *Biochem. J.* 113: 299–305 (1969), or with 35-S by growth in 35-S methionine. The labeled cells were dissolved in solubilization buffer (1% (v/v) Triton X-100, 150 mM NaCl, 5 mM EDTA, 25 mM Tris-HCl, pH 7.5). Four parts of labeled extract were mixed in a vessel with one part solubilization buffer containing 50 mg/ml bovine serum albumin, to give a final concentration of 10 mg/ml BSA. The balls coated with monoclonal antibody were added to the vessel and were incubated four hours on ice with shaking. Labeled antigen was pipetted from the vessel and the balls with rinsed four times with solubilization buffer. The balls were then removed, placed in individual tubes with 100 microliter Laemmli SDS gel sample buffer, and were incubated three minutes in boiling water. The balls were removed and the samples were run on an SDS gel with appropriate standards.

Immunoprecipitation tests on the antibodies indicated that five of them (454C11, 452F2, 520C9, 741F8, and 759E3) all bind a monomeric protein of about 200 K daltons found in cancerous breast tissue. Two of the five (520C9 and 741F8), are believed to recognize the same epitope on the 200 K dalton protein. 454C11 and 759E3 bind a second epitope on the same antigen, and 452F2 binds a third epitope on the same antigen. Four of the antibodies (41B4, 87H7, 452E12, 457D7) bound to a 230,000 dalton intracellular antigen. Seven antibodies (2G3, 200F9, 203E2, 245E7, 369F10, 697B3 and 788G6) bound to high molecular weight mucins (HMW). Two antibodies (51C3 and 454A12) bound to transferrin receptors in the form of a 97,000 dalton antigen. Neither 451C3 nor 454A12 blocked binding of transferrin to the receptor. The antigen binding characteristics of the monoclonal antibodies according to the invention are summarized in Table 7.

TABLE 7

| MAB | Antigen |
| --- | --- |
| 2G3 | HMW Mucin |
| 9C6 | 70 K |
| 32A1 | |
| 33F8 | 66 K |
| 35E10 | 80 K |
| 41B4 | 240 K |
| 87H7 | 230 K |
| 106A10 | 55 K a |
| 113F1 | 40, 60, 100, 200 K Very Diffuse |
| 120H7 | HMW Mucin |
| 140A7 | Glycolipid (pentasaccharide) |
| 200F9 | HMW Mucin |
| 203E2 | HMW Mucin |
| 219F3 | |
| 245E7 | HMW Mucin |
| 254H9 | |
| 260F9 | 55 K b |
| 266B2 | 55 K b |
| 317G5 | 42 K c |
| 369F10 | HMW Mucin |
| 387H9 | 40 K |
| 421E8 | |
| 451C3 | Transferrin receptor |
| 452E12 | 240 K |
| 452F2 | 200 K |
| 454A12 | Transferrin receptor |
| 454C11 | 200 K |
| 457D7 | 240 K |
| 520C9 | 200 K |
| 650E2 | 42 K c |
| 697B3 | 200 K |
| 759E3 | 200 K |
| 788G6 | HMW Mucin | a = Different epitope than that bound by 260F9 and 266B2
b = Different epitope than that bound by 10610; both 260F9 and 266B2 appear to bind to same epitope
c = Cross block each other

ANTIBODY ISOTYPE

Antibody isotype was determined as follows: A grid of 5-mm squares is lightly drawn in pencil on the nitrocellulose sheet and 1-ml droplets of antiisotype sera (Litton Bionetics, Kensington, Md., rabbit antisera to mouse κ, λ, α, γ1, γ2a, γ2b, γ3, and μ chains) are applied so that each row of squares receives one spot of each heavy and light chain reagent. The sheet is incubated one hour at room temperature in a moist chamber, rinsed quickly in PBS-BSA, containing 1% (w/v), and left overnight in PBS-BSA at 4° C. Strips are cut apart with a scissors and may be stored at 4° C. in PBS-BSA containing 0.02% sodium azide. Alternatively, strips may be air-dried and stored desiccated at 4° C. A series of small tubes is prepared containing 3 ml hybridoma culture supernatant or supernatant diluted with PBS-BSA. 1:10 dilutions are generally successful; and some supernatants can be diluted as much as 1:200. A nitrocellulose strip is incubated in each tube for one hour at room temperature. The strips are rinsed three times in PBS-BSA and incubated for one hour at room temperature in diluted rabbit anti-mouse-horseradish peroxidase. The strips are rinsed twice in PBS-BSA and twice in Tris buffer. The strips are placed in Tris buffer containing diaminobenzidine and hydrogen peroxide until sufficient color develops on the anti-isotype spots (usually 3–4 minutes). The antibody isotypes are indicated in Table 8.

TABLE 8

| Isotype of Imaging MABs | |
| --- | --- |
| MAB | Isotype |
| 2G3 | G1 |
| 9C6 | M |
| 32A1 | G1 |
| 33F8 | G1 |
| 35E10 | M |
| 41B4 | G1 |
| 87H7 | G1 |
| 106A10 | G1 |
| 113F1 | G3 |
| 120H7 | M |
| 140A7 | M |
| 200F9 | G1 |
| 203E2 | G1 |
| 219F3 | G1 |
| 245E7 | G1 |
| 254H9 | M |
| 260F9 | G1 |
| 266B2 | G1 |

TABLE 8-continued

Isotype of Imaging MABs

| MAB | Isotype |
| --- | --- |
| 317G5 | G1 |
| 369F10 | M |
| 387H9 | G1 |
| 421E8 | G1 |
| 451C3 | G1 |
| 452E12 | G1 |
| 452F2 | G1 |
| 454A12 | G1 |
| 454C11 | G2A |
| 457D7 | G1 |
| 520C9 | G1 |
| 650E2 | G1 |
| 697B3 | G1 |
| 741F8 | G1 |
| 759E3 | G1 |
| 788G6 | G1 |

Samples of the hybridomas that produce the claimed monoclonal antibodies are deposited in the Collection of In Vitro International, 7885 Jackson Road, Suite 4, Ann Arbor, Mich. 48103, USA.

EXAMPLE I

This example shows one method for the labeling of antibodies according to the invention with radioisotopes of iodine, either 125-iodine or 131-iodine using a method known to iodinate tyrosine residues.

Monoclonal antibodies according to the invention may be labeled by the following micro method: 0.1 milligram of the purified monoclonal antibody is labeled with 10 millicurie amounts of 125 iodine as follows: A one inch, 21 gauge needle is inserted partially through the septum of a 3 ml vial and a 3.0 ml disposable syringe barrel packed with glass wool is attached to the needle. The monoclonal antibody in 0.1N NaCl preferably not exceeding 0.2 ml in volume, is added with a tuberculin syringe equipped with a 20 gauge needle that has been prerinsed with borate buffer. The sodium 125-iodine solution preferably not exceeding 0.2 to 0.3 ml in volume is added with a syringe attached to an 18 gauge needle pre-rinsed with buffer. The mixture is agitated briefly to mix the protein and 125 iodine solutions. Final dilution of the iodine chloride is made by mixing 0.2 ml of 125-iodine chloride at approximately $1.25 \times 10^{-5}$ molar (M) with a specific activity of 10 millicuries per mole. After approximately one minute, an excess of 6.25% solution of human serum albumin or animal albumin such as bovine serum albumin is added to the solution. The labeled antibody is passed through an appropriate column to remove unbound radioactive iodine; an ion exchange resin or gel filtration medium such as Sephadex G-25 may be used. For a Sephadex column purification, after passage of the labeled antibody through the resin at the rate of about one ml per minute, the resin is rinsed with an additional 1 to 1.5 mls of the above-mentioned human albumin solution.

EXAMPLE II

The monoclonal antibodies according to the invention may also be iodinated by linking agents. This example describes the radioactive labeling of the monoclonal antibody with an iodinated imidination reagent. The imido ester methylparahydroxybenzimidate HCL (MPHBIM) is synthesized according to the method described by Wood et al., "The Radioactive Labeling of Protein With an Iodinated Imidination Reagent", *Analytical Biochem.* 69: 339–349 (1975). The MPHBIM is iodinated as follows: 3.7 ml of MPHBIM is dissolved in 1 ml of 50 millimolar mM sodium borate buffer pH 8.5 to obtain a 20 mM MPHBIM stock solution. 1.0 ml of 40 mM sodium iodine followed by 10 microliters of sodium iodide-125 solution having a specific activity of approximately 2 millicuries per mole is added to one ml of the MPHBIM stock solution. One ml of 40 millimolar chloramine T is added with rapid mixing. The mixture is kept for approximately 15 minutes at 20°–22° C. and then 0.1 ml of 1.0 molar β-mercaptoethanol is added to reduce the chloramine T and residual iodine. The pH of the solution is subsequently lowered toward neutrality by adding 20 microliters of 1.0 molar acetic acid and a floculant white precipitate forms. Unreacted MPHBIM iodide and chloramine T remain soluble. The precipitate of the iodinated amino ester is collected by centrifugation at 10,000 rpm for five minutes, dissolved in two mls of 50 mM sodium borate buffer, pH 8.5 at 37° C. Iodination of the antibody is carried out as follows: Twenty milligrams of purified antibody is suspended in one ml of 4 mM iodinated linker, 50 mM sodium borate buffer at pH 9.5. The reaction is carried out at 37° C. for a period of time sufficient to achieve the desired amount of binding. Under these conditions the radioactive label is incorporated onto the antibody at a rate of about 1–2% per hour with a maximum incorporation of approximately 30% of the iodine-125 label. Unreacted linker may be removed by dialysis against 0.15 molar sodium chloride containing a 5 mM sodium phosphate at a pH 7.4.

EXAMPLE III

Labeling of the Monoclonal Antibody with Chelating Groups-DTPA

The monoclonal antibodies may be labeled with 111-In using the chelating agent diethylenetriaminepentaacetic acid (DTPA) anhydride according to the method of Hnatowich et al., *Science* 220: 613–615 (1983) which is herein incorporated by reference. Antibody 113F1, is prepared at 11 milligrams per ml dialysed into NaHCO$_3$ at pH 7. One mg DTPA cyclic anhydride was dissolved in 10 ml CHCl$_3$. Forty $\mu$l of this solution was delivered into 5 m/glass test tube and the CHCl$_3$ was evaporated with a strean of N$_2$. One-hundred microliters of 113F1 (1.1 milligrams protein) was added to the tube containing 4 micrograms of anhydride and the tube was vortexed briefly. After one minute, 5 microliters of 111-In (having a specific activity of about $3.28 \times 10^{10}$ cpm/ml) in 0.5 molar sodium acetate at pH 5.8 was added. Two PD10 (Pharmacia) columns were prepared with 20 milliliters of phosphate buffered saline 1% bovine serum albumin. The samples were run on the PD10 columns with 2.2 milliliters of void volume. A 2.5 milliliter protein peak and 2.5 milliliters small molecule peak were found eluting with the PBS 1% BSA. The control was a 100 microliter sample of 113F1 together with 4 microliters of one microgram/microliter DTPA, not the anhydride, and 5 microliters of 111-In. The DTPA anhydride labeled 113F1 protein peak contained 75% of the counts and the small molecule peak/fraction contained approximately 25% of the counts. In the control approximately 92% of the counts remained in the small molecule fraction.

EXAMPLE IV

Labeling of Antibody With Various Activities of Indium

Monoclonal antibody 113F1 from the previous experiment was diluted in 50 millimolar NaHCO$_3$ pH 7 to concentrations of 100, 10 and 1 micrograms per 100 μl. One hundred μl of each dilution of 113F1 was added to 4 μg DTPA anhydride in a glass tube as in Example III. 111-In was diluted in 0.5 molar sodium acetate pH 5.8 to 100 microcuries per 10 μl. One hundred micrucuries 111-In in 10 microliters solution was added to the tubes containing the antibody. The mixture was treated as in Example III. Seventy-six percent of the counts were found in the protein fraction of the one microgram per 100 microliter dilution and 86% of the counts were found in the 100 microgram per 100 microliter dilution.

EXAMPLE V

Labeling of Anitbody 245E7 with 111-Indium

This example shows the labeling of another antibody according to the invention with 111-In.

1 mg DTPA cyclic anhydride was dissolved in 10 mls dry CHCl$_3$. 40 μl of the dissolved DTPA anhydride was placed in a 5 ml glass tube and was evaporated with N$_2$ to yield about 4 μg DTPA cyclic anhydride coated on the inside of the tube.

100 μl of antibody 245E7 at a concentration of 15 mg/ml in 50 mM NaHCO$_3$ pH 7 was added to the DTPA cyclic anhydride. The tube was briefly vortexed and left to stand for about one minute forming the DTPA-245E7 complex.

Five test samples were made up as follows:
(1) 10 μl DTPA-245E7 complex in 90 μl NaHCO$_3$
(2) 10 μl DTPA-245E7 complex in 90 μl NaHCO$_3$
(3) 10 μl 245-E7 in 90 μl NaHCO$_3$
(4) 10 μl 245E7 in 90 μl NaHCO$_3$
(5) 10 μl 245E7 in 90 μl NaHCO$_3$ and 0.4 μg DTPA not anhydride form.

111-In was diluted to a specific activity of 100 cpm/μl in 0.5 sodium acetate pH 5.8. 10 ml of this 111-In solution was added to each tube. 10 μg DTPA in the non-anhydride form was added to tubes 2 and 4. The contents of each tube were run on a PD10 column equilibrated with NaHCO$_3$ as in Example III. Samples were collected and the protein and small molecule peaks were counted in a liquid scintillation counter using conventional methods. The results are shown in Table 9.

TABLE 9

| Tube Fraction | CPM | % Total Counts |
|---|---|---|
| *P | 3263 | 77 |
| +SM | 964 | 23 |
| P | 3050 | 75 |
| SM | 998 | 25 |
| P | 267 | 42 |
| SM | 364 | 58 |
| P | 391 | 24 |
| SM | 2897 | 76 |
| P | 778 | 19 |
| SM | 3295 | 81 |

*Protein
+Small molecules

The results indicate that 77% of the 111-In bound to DTPA labeled 245E7. Subsequent addition of excess free DTPA does not remove indium from the DTPA-245E7 antibody complex. Sample 3 shows that indium does not non-specifically bind to the antibody in any appreciable amount; however, the indium appears to be retained on the column rather than eluting with the small molecule fraction. DTPA added before or after indium results in the indium eluting in the small molecule peak.

EXAMPLE VI

Uptake of 111-Indium Labeled Monoclonal Antibodies to Breast Tumor Tissues

This example shows that 111-In labeled monoclonal antibodies are efficiently bound by human breast tumor tissues.

Six anti-breast cancer tumor monoclonal antibodies 113F1, 245E7, 260F9, 280D11, 2G3, 266B2, and a negative control MOPC21, were covalently linked to DTPA anhydride by the method described in Example III above. The antibody-DTPA complex was radiolabeled by chelation with 111-In at a specific activity of about 1μ Ci/μg. The 111-In labeled antibody was purified when necessary on a 0.4×17 cm column of Sephadex G50 to a radiochemcial purity of about 90%. Two non-breast specific antibodies, anti-carcinoembryonic antigen monoclonal antibody (anti-CEA) obtained from Medi-Physics, Emeryville, Calif. and anti-prostatic acid phosphatase antibody (anti-PAP) obtained from New England Nuclear Corporation, Boston, Mass.) were labeled in the same manner as the anti-breast cancer tumor antibodies and served as positive binding controls. Human breast and colorectal tumor tissues were obtained immediately after surgery and were placed in fresh Eagles Minimal Essential Media (MEM) supplemented with 10% fetal calf serum, non-essential amino acids, glutamine, penicillin and streptomycin (MEM) for transportation. Fresh tissue was used within three hours of receipt while cryopreserved tissue was maintained in MEM at −70° C. The tissues were sectioned manually with surgical blades into 1.0±00.2 mm cubes and checked for size accuracy using an ocular micormeter. Using sterile techniques, the tissue cubes were transferred to a 96-well microtiter plate containing 200 μl of MEM and either 1.0 or 10 μg of 111-In-labeled antibody. The tissues were incubated from 1-24 hours at 37° C. in a 5% CO$_2$ water-jacketed incubator. Following incubation, the media was carefully removed using an automatic pipetter with minimal disruption of the tissue, and fresh media was added. Following incubation for an additional 20 minutes, the media was again replaced and the tissue was incubated for another 20 minutes. After this last wash, the media was removed and the tissue transferred to a dry tared weighing paper. Tissues were dried at 70° C. for 20 minutes and were then weighed and placed in test tubes for counting in a NaI well counter. The results are reported as the percent of applied radioactivity in tissue per unit weight of dried tissue. Small differences in the size of each tissue cube were corrected.

Specificity of Binding

To establish that the accumulation of radiolabeled antibody in tumor tissue is due to specific binding rather than non-specific adsorption, radiolabeled anti-CEA and anti-PAP antibodies, used as controls, were incubated with fresh and cryopreserved human colorectal tumor tissue which expresses CEA. FIG. 1 shows the percent incorporation of radioactivity vs. incubation time at 37° C. for both antibodies, each at 1 μg and 10 μg/well, for one tumor tissue.

At the 1 μg/well concentration, the anti-PAP antibody shows little incorporation at any time. The anti-CEA antibody by contrast shows about a 20 fold increased accumulation. At 10 μg/well, the difference in radioactivity accumulation for the specific and non-specific antibodies is much less indicating saturation of the antigenic sites.

Specific binding of the anti-CEA control antibody was further demonstrated by a competitive binding study. Tumor tissue was preincubated with saturating levels (25 μg) of unlabeled anti-CEA antibody for 17 hours prior to the normal assay using 1 μg of labeled anti-CEA antibody. Control wells did not receive the unlabeled antibody. As shown in Table 10, in the case of the non-specific antibody, there was essentially no change in tissue accumulation of radioactivity with preincubation whereas in the case of the specific antibody, a large decrease in accumulation occurred in the tissue preincubated with the unlabeled anti-CEa antibody.

TABLE 10

Binding of radiolabeled anti-CEA and anti-PAP to colorectal tumor tissue without preincubation with unlabeled anti-CEA antibody

| Antibody | Weight of unlabeled anti-CEA antibody per well (μg) | Radioactivity Bound* (%) |
| --- | --- | --- |
| Anti-CEA | 0 | 28.3 |
|  | 25 | 1.2 |
| anti-PAP | 0 | 1.3 |
|  | 25 | 0.8 |

*Mean value (n = 3)

Selectivity of Binding

A panel consisting of labeled anti-CEA and anti-PAP and the six anti-breast cancer tumor monoclonal antibodies was tested using two human breast tumor tissues. Replicate measurements of binding of the same antibody in the same tissue show only small variations, while the variation in binding of the same antibody in different tissues or different antibodies in the same tissue is far larger, as shown in FIG. 1.

The antibody 113F1 showed only modest binding in one of the tumor tissues but showed the highest degree of binding in the other. Although as expected, the anti-CEA antibody showed the same degree of binding as the anti-PAP antibody in one of the breast tumor tissue, the former showed increased binding with respect to the latter in the other tumor tissue tested.

Also in FIG. 1 (left panel) is presented the results of a repeat measurement of the same antibodies and the same tissue analyzed initially (solid bars) and three days later (cross hatched bars). Although there are slight differences in the level of uptake of individual antibodies, the order, ranked according to antibody accumulation, is unchanged.

EXAMPLE VII

Nineteen 8 week old female nude mice were implanted with MX-1 tumors subcutaneously in the right dorsal flank. The mice were furnished with food and water ad libitum. At 14 days after implant when the subcutaneous tumors had reached a size of approximately 0.5 cm$^3$, the water was replaced with water containing 0.1% KI.

Monoclonal antibody 260F9 was labeled with 125-I 1,3,4,6Tetrachloro-3α,6α-diphenyl glycouril (Iodogen TM) as follows. 10 μl of Iodogen TM was placed in a sterile glass test tube and 1 UCi of 125-I as NaI salt with a specific activity of about 17 Ci/mg (New England Nuclear) was added to the iodogen. Monoclonal antibody 260F9 in phosphate buffered saline, without azide was added to the Iodogen TM 125-I to label the antibody at a specific activity of 5 μCi/μg antibody.

Monoclonal antibody MOPC21 was labeled in the same manner and served as a control. Approximately 2 μg of labeled antibody containing approximately 10 μCi I-125 was administered to each mouse. The labeled antibody was administered in a volume of approximately 0.1 ml PBS containing 1% BSA, via the mouse tail vein. Four days after administration of the labeled antibody the mice were exsanguinated by eye puncture. The blood was heparinized, centrifuged and the blood plasma was retained. The organs were disected, chopped into approximately 1 MM$^3$ pieces and were washed in saline to remove excess counts. The chopped tissue was weighed and the radio activity was measured in an LKB gamma counter.

The tissues of six mice treated with iodinated MPOC21 served as controls. The tissues of 13 mice treated with I-125 labeled 260F9 served as test tissues. Counts per minute per gram (cpm/gm) tissue or tumor were determind and an index of uptake was determined by the ratio of cpm/gm tumor to cpm/gram organ (T/O ratio).

Table 11 shows the T/O ratio for 260F9 at 10 μCi I-125 for MX-1 tumors in each animal tested. Table 12 shows the T/o ratio for MOPC21 at 10 μCi I-125 for MX-1 tumors in each animal tested. Table 13 shows the means and standard deviation for all tested animals.

TABLE 11

| | T/O Ratios for 260F9 at 10 μCi MX-1 Tumors | | | | | | | | | | | | |
| --- | --- | --- | --- | --- | --- | --- | --- | --- | --- | --- | --- | --- | --- |
| | #242 | #243 | #244 | #317 | #318 | #319 | #391 | #392 | #393 | #377 | #362 | #536 | #534 |
| Plasma | 3.01 | 7.62 | 2.64 | 1.26 | .92 | 1.78 | 3.45 | 1.88 | 1.92 | 5.10 | .70 | 2.89 | 1.90 |
| Ribs | 45.00 | 43.62 | 35.93 | 23.08 | 14.27 | 28.51 | 31.36 | 20.89 | 27.43 | 60.5 | 10.00 | 18.06 | 17.3 |
| Lungs | 12.10 | 23.87 | 8.82 | 6.24 | 3.78 | 7.35 | 13.27 | 10.44 | 11.29 | 15.50 | 2.20 | 6.28 | 11.20 |
| Liver | 15.65 | 36.14 | 11.02 | 6.16 | 6.55 | 7.40 | 10.78 | 7.23 | 9.60 | 31.80 | 3.60 | 6.28 | 6.60 |
| Spleen | 9.41 | 14.06 | 14.70 | 5.54 | 5.06 | 7.00 | 14.38 | 7.52 | 9.14 | 9.40 | 3.70 | 7.05 | 7.30 |
| Kidney | 11.61 | 42.17 | 11.28 | 8.20 | 6.69 | 12.05 | 13.80 | 15.67 | 12.80 | 18.30 | 4.30 | 9.63 | 8.60 |
| Heart | 10.75 | 48.65 | 15.65 | 6.93 | 8.45 | 16.94 | 38.33 | 17.09 | 14.77 | 29.00 | 3.60 | 28.90 | 11.90 |
| G1 | 57.60 | 105.42 | 48.50 | 29.47 | 18.34 | 37.71 | 49.29 | 18.80 | 19.20 | 50.00 | 16.50 | 22.23 | 63.30 |
| Carcass | 25.10 | 84.70 | 29.30 | 15.74 | 10.35 | 17.45 | 23.00 | 20.00 | 20.00 | 26.00 | 8.50 | 9.00 | 15.00 |

TABLE 12

| | T/O Ratios of M0PC21 at 10 μCi - MX-1 Tumors | | | | | |
| --- | --- | --- | --- | --- | --- | --- |
| | #270 | #312 | #394 | #375 | #376 | #535 |
| Plasma | .36 | .30 | .17 | .14 | .15 | .26 |
| Ribs | 4.85 | 5.72 | 1.86 | 2.20 | 2.00 | 2.89 |
| Lungs | 2.70 | 3.37 | 2.90 | 1.70 | 1.00 | 1.18 |
| Liver | 3.71 | 2.75 | 1.88 | 1.50 | 1.40 | 1.86 |

TABLE 12-continued

| T/O Ratios of M0PC21 at 10 μCi - MX-1 Tumors | | | | | | |
|---|---|---|---|---|---|---|
| | #270 | #312 | #394 | #375 | #376 | #535 |
| Spleen | 5.46 | 7.66 | 2.43 | 1.70 | 2.00 | 2.89 |
| Kidney | 3.96 | 2.30 | 2.16 | 2.00 | 1.20 | 1.86 |
| Heart | 3.15 | 2.42 | 1.30 | 1.80 | 1.00 | 2.00 |
| GI | 13.25 | 8.99 | 3.70 | 3.90 | 4.70 | 8.67 |
| Carcass | 3.60 | 4.30 | 3.00 | 2.60 | 2.00 | 2.89 |

TABLE 13

| | Tumor/Organ Ratios | | | |
|---|---|---|---|---|
| | 260F9 | | M0PC21 | |
| | Mean | Std. Dev. | Mean | Std. Dev. |
| Plasma | 2.70 | 1.89 | .23 | .09 |
| Ribs | 28.92 | 14.29 | 3.25 | 1.64 |
| Lung | 10.18 | 5.60 | 2.14 | .98 |
| Liver | 12.22 | 10.15 | 2.18 | .89 |
| Spleen | 8.79 | 3.60 | 3.69 | 2.36 |
| Kidney | 13.47 | 9.39 | 2.25 | .92 |
| Heart | 19.30 | 13.23 | 1.95 | .78 |
| GI | 41.26 | 25.34 | 7.20 | 3.78 |
| Carcass | 23.40 | 19.56 | 3.07 | .80 |

EXAMPLE VIII

Prior to exsanguination two mice treated with labeled 260F9 and one mouse treated with labeled MOPC21 according to Example VII were imaged using a Searle Pho-gamma camera with a pinhole collimnator. Raw data were collected and computor enhanced. The images of the treated and control mice are shown in FIG. 3.

Figure 3:
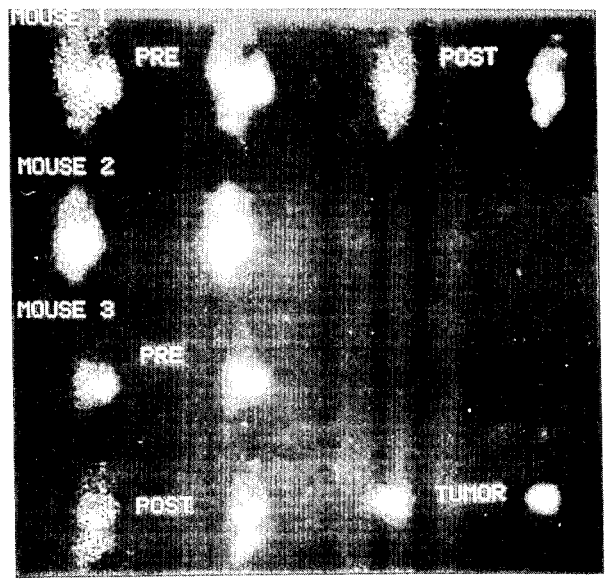

In the first line of FIG. 3, from left to right, are images of a tumor bearing mouse treated with 125-I-labeled 260F9 prior to surgical removal of the tumor, raw data; a computor-enhanced image of the same mouse; an image of of the mouse, post surgical, raw data; and a computer-enhanced image of the same mouse, post surgical. A prominent area of localization of detectable radiation is found in a position corresponding to the MX-1 tumor, on the dorsal right flank of the mouse treated with 125-I-labeled 260F9.

In the second line of FIG. 3 from left to right are images of a tumor bearing mouse treated with 125-I labeled MOPC21, an antibody not specific for the tumor used as a control, raw data, and a computor enhanced image of the same mouse. There is no corresonding area of localization of detectable radiation on the dorsal right flank as in the mouse treated with 125-I labeled 260F9. Furthermore, the distribution of label in the control mouse appears to correspond to the distribution of label in the post-surgical mouse treated with 125-I-labeled 260F9.

In the third line of FIG. 3, from left to right are images of a tumor bearing mouse treated with 125-I labeled 260F9, pre-surgical, raw data, and a computer enhanced image of the same mouse. A prominent area of localization of detectable radiation is found on the right dorsal flank of the mouse in a position corresonding to the MX-1 tumor.

In the fourth line of FIG. 3, from left to right are images of the tumor bearing mouse from line 3, post surgical, raw data; a computer enhanced image of the same mouse, post surgical; an image of the tumor excised from the same mouse, raw data and a computer enhanced image of the same excised tumor. A significant amount of the labeled tumor-specific antibody is shown to have localized in the tumor. The amount of detectable tumor-specific antibody remaining in the mouse post surgically appears to be less than the amount of detectable antibody in the control mouse in line two in this limited sample.

The monoclonal antibodies according to the invention, after derivatization with a labeling moiety, have a number of uses. The immunoimaging monoclonal antibodies may be used in diagnosis of primary malignant breast tumors. Patients presenting with masses indicating a possibility of malignant breast tumors presently routinely undergo a series of diagnostic mammographic examinations. In additio to mammography, the immunoimaging antibodies according to the invention may be administered subcutaneously or intravenously to determine whether the mass is positive for uptake of the labeled antibody according to the invention. Accumulation of the labeled antibody would serve as an additional indication suggesting the need for a biopsy or more extensive surgical intervention.

The labeled monoclonal antibodies according to the invention also have a clear use in assaying the clinical prognosis of patients who have had mastectomies or lumpectomies for removal of malignant breast tumors. Conventionally, the axillary lymph nodes of such patients are disected to determine the extent of dissemination of the malignancy. Under current practice, patients with positive nodes receive a course of adjuvant chemotherapy. Axillary node sampling is an invasive procedure requiring general anesthesia. It entails all the risks of any major surgical procedure including infection and reaction to anesthetics, and requires a significant post operative period of pain, recovery and healing.

The monoclonal antibodies according to the invention and the derivatives thereof, can be used as a non-invasive method for determining the nodal involvement of a breast malignancy and may serve as an adjunctive procedure to conventional nodal dissection or as a replacement therefor.

The utility of radiolabeled monoclonal antibodies has been shown, at least in a preliminary manner in a number of clinical studies. McKenzie et al. "Immunoscintigraphy for Detection of Lymph Node Metastases From Breast Cancer" Lancet No. 8414: 1245 (1984) have shown that subcutaneous interdigital injection of an I-131 labeled monoclonal antibody specific for a human malignant breast tumor, can be used to confirm the prsence of metastases in patients who were already suspected to have tumors involving axillary lymph nodes, and to detect tumors in lymph nodes where the presence of tumor had not been suspected. Using a Toshiba GCA402 gamma counter camera and a high energy parallel hole collimator-computerized equalization with an Informatek Simes 4 computer, at 24 hours post-injection, immunoscintigraphy was more sensitive than conventional clinical examination for the detection of metastases in draining nodes.

Breast tumor localization with the labeled derivatives of monoclonal antibodies according to the invention by intravenous administration, is also a clear alternative to the subcutaneous administration route. In this method, the radiolabeled monoclonal antibody is introduced into the patient in a solution appropriate for IV administration such as 0.15M NaCl with 1% human serum albumin. The radiolabeled monoclonal antibody is injected preferably using a venous catheter in a volume of saline over an approximately 30 minute period.

In both subcutaneous and inravenous administration methods, the patient is tested for allergy to the normal antibody of the animal from which the monoclonal producing hybridoma was produced. In general, if the monoclonal antibody is derivatized with a radioisotope of iodine, the patient is pre-treated with Lugols iodine-solution to block thyroid uptake in 131-I, and premediated with promethazine and prednisolone before administration of the immunoimaging monoclonal antibody. Patients are scanned over a period of hours to days after administration of the immunimaging monoclonal antibody. Scanning methods for radioisotopic imaging including appropriate control procedures such as subtraction analysis with non-specific antibody are known to those skilled in the art of nuclear medicine and include computer assitsed photoscanning and computer assisted tomoscintigraphy.

Other clinical uses of the labeled monoclonal antibodies according to the invention are clear to those skilled in the art of breast cancer patient management. Such uses include the use of the labeled monoclonal antibodies to monitor the response of metastatic tumors to therapy using various therapeutics including chemotherapeutics, immunotoxins, immunodrugs or lymphokines.

The labeled monoclonal antibodies according to the invention may also be used to detect the presence of life endangering highly morbid metastases at a time prior to their symptomatic manifestation early enough to permit preventive or ameliorating radiotherapy. The most highly selective antibodies according to the invention may also be labeled to determine the distribution or locatization of lack thereof of the monoclonal antibody in the normal tissues of patients thus providing a basis of identifying breast cancer specific monoclonal antibodies that may be advantageously used as components for antibody based therapeutics such as immunotoxins or immunodrugs for the treatment of malignant breast tumors.

These and other aspects of the invention will be apparent to those ordinarily skilled in the art to which this application pertains.

The monoclonal antibody-producing hybridomas listed below were deposited with the American Type Culture Collection (ATCC) or Invitro International Inc. (IVI) under the terms of the Budapest Treaty on the International Recognition of the Deposit of Microorganisms for the Purposes of Patent Procedure and the Regulations thereunder (Budapest Treaty). This assures maintenance of the viable culture for 30 years from date of deposit. The hybridomas will be made available by ATCC or IVI under the terms of the Budapest Treaty, and subject to an agreement between applicants and ATCC or IVI which assures unrestricted availability upon issuance of the pertinent U.S. patent. Availability of the deposited strains is not to be construed as a license to practice the invention in contravention of the rights granted under the authority of any government in accordance with its patent laws.

Each hybridoma designation listed in the left column corresponds to the monoclonal antibody producing the designated monoclonal antibody.

| Cell Line Designation | IVI Accession Number |
| --- | --- |
| 9C6 | IVI-10056 |
| 41B4 | IVI-10057 |
| 87H7 | IVI-10059 |
| 106A10 | IVI-10060 |
| 120H7 | IVI-10061 |
| 200F9 | IVI-10062 |
| 254H9 | IVI-10063 |
| 421E8 | IVI-10064 |
| 32A1 | IVI-10066 |

-continued

| | |
| --- | --- |
| 35E10 | IVI-10067 |
| 140A7 | IVI-10069 |
| 203E2 | IVI-10070 |
| 219F3 | IVI-10072 |
| 387H9 | IVI-10073 |
| 452E12 | IVI-10074 |
| 454A12 | IVI-10075 |
| 457D7 | IVI-10076 |
| 697B3 | IVI-10077 |
| 741F8 | IVI-10078 |
| 759E3 | IVI-10079 |
| 788G6 | IVI-10080 |
| 451C3 | IVI-10081 |
| 452F2 | IVI-10082 |
| 650E2 | IVI-10083 |

| Cell Line Designation | ATCC Accession Number |
| --- | --- |
| 2G3 | HB-8491 |
| 33F8 | HB-8697 |
| 113F1 | HB-8490 |
| 245E7 | HB-8489 |
| 266B2 | HB-8486 |
| 317G5 | HB-8485 |
| 369F10 | HB-8682 |
| 454C11 | HB-8484 |

What is claimed is:

1. A method for imaging breast tumors, comprising the steps of:
   (a) producing an immunoimaging composition comprising covalently binding an imaging moiety to a murine monoclonal antibody suitable for imaging breast tumors, said murine monoclonal antibodies having the properites of not binding to blood cells or human mammary tumor virus, a breast tumor binding range of at least 0.25, or has a breast cancer cell line range of greater than or equal to 0.25, a selectivity equal to or less than 0.09, a G or M isotype, and are selected from the group consisting of 2G3, 9C6, 32A1, 35E10, 87H7, 106A10, 120H7, 140A7, 260F9, 203E2, 219F3, 452E12, 454A12, 650E2, 697B3, 759E3, and 788G6;
   (b) administering said imaging composition to a patient; and
   (c) detecting a signal produced by said imaging moiety.

2. The method as described in claim 1, wherein said detectable imaging moiety is bound to said monoclonal antibody using N-chloro-p-toluenesulfonamide or tetrachloro-3α, 6α-diphenylglycouril.

3. The method as described in claim 2, wherein said imaging moiety is bound to a linker that is bound to said monoclonal antibody.

4. The method as described in claim 3, wherein said linker is methyl-p-hydroxybenzimidate or N-succinimidyl-3-(4-hydroxyphenyl)propionate.

5. The method as described in claim 4, wherein said imaging moiety is bound to said murine monoclonal antibody by a chelating agent.

6. The method as described in claim 5, wherein said chelating agent is diethylenetriaminepentaacetic acid anhydride or ethylenetriaminetetraacetic acid.

7. The method as described in claim 6, wherein said imaging moiety is selected from the group consisting of:
   (a) fluorochromes;
   (b) radioactive iostypes;
   (c) radiopaque substances; and
   (d) NMR detectable substances.

8. The method as described in claim 7, wherein said radio isotope is selected from the group consisting of $^{123}$Iodine, $^{131}$Iodine, $^{111}$Indium and $^{99}$Technetium.

9. The method as described in claim 2, wherein said imaging agent is administered to a patient with a carrier suitable for parenteral administration.

* * * * *